(12) United States Patent
Ozcan et al.

(10) Patent No.: US 12,270,068 B2
(45) Date of Patent: Apr. 8, 2025

(54) SYSTEMS AND METHODS FOR THE EARLY DETECTION AND CLASSIFICATION OF LIVE MICROORGANISMS USING TIME-LAPSE COHERENT IMAGING AND DEEP LEARNING

(71) Applicant: THE REGENTS OF THE UNIVERSITY OF CALIFORNIA, Los Angeles, CA (US)

(72) Inventors: Aydogan Ozcan, Los Angeles, CA (US); Yair Rivenson, Los Angeles, CA (US); Hongda Wang, Los Angeles, CA (US); Hatice Ceylan Koydemir, Los Angeles, CA (US); Yunzhe Qiu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 342 days.

(21) Appl. No.: 17/793,926

(22) PCT Filed: Jan. 27, 2021

(86) PCT No.: PCT/US2021/015321
§ 371 (c)(1),
(2) Date: Jul. 19, 2022

(87) PCT Pub. No.: WO2021/154876
PCT Pub. Date: May 8, 2021

(65) Prior Publication Data
US 2023/0060037 A1 Feb. 23, 2023

Related U.S. Application Data

(60) Provisional application No. 62/966,965, filed on Jan. 28, 2020.

(51) Int. Cl.
*C12Q 1/04* (2006.01)
*G02B 21/26* (2006.01)
(Continued)

(52) U.S. Cl.
CPC .............. *C12Q 1/04* (2013.01); *G02B 21/26* (2013.01); *G02B 21/365* (2013.01);
(Continued)

(58) Field of Classification Search
CPC ........ C12Q 1/04; G02B 21/26; G02B 21/365; G03H 1/0005; G03H 2001/005;
(Continued)

(56) References Cited

U.S. PATENT DOCUMENTS 4,724,215 A * 2/1988 Farber ................... G01N 35/00
348/82
10,365,214 B2 7/2019 Ozcan et al.
(Continued)

FOREIGN PATENT DOCUMENTS

EP 3867637 8/2021
WO WO 2013/142219 9/2013
(Continued)

OTHER PUBLICATIONS

Chapelais-Baron et al., "Colony analysis and deep learning uncover S-hydroxyindole as an inhibitor of gliding motility and iridescence in Cellulophaga lytica." Microbiology vol. 164(3), Mar. 1, 2018 (Mar. 1, 2018) (Year: 2018).*
(Continued)

*Primary Examiner* — Wesley J Tucker
(74) *Attorney, Agent, or Firm* — VISTA IP LAW GROUP LLP

(57) ABSTRACT

A system for the detection and classification of live microorganisms in a sample includes a light source and an incubator holding one or more sample-containing growth
(Continued)

plates. A translation stage moves the image sensor and/or the growth plate(s) along one or more dimensions to capture time-lapse holographic images of microorganisms. Image processing software executed by a computing device captures time-lapse holographic images of the microorganisms or clusters of microorganisms on the one or more growth plates. The image processing software is configured to detect candidate microorganism colonies in reconstructed, time-lapse holographic images based on differential image analysis. The image processing software includes one or more trained deep neural networks that process the time-lapsed image(s) of candidate microorganism colonies to detect true microorganism colonies and/or output a species associated with each true microorganism colony.

24 Claims, 21 Drawing Sheets

(51) Int. Cl.
  *G02B 21/36* (2006.01)
  *G03H 1/00* (2006.01)
  *G06V 10/10* (2022.01)
  *G06V 10/82* (2022.01)
  *G06V 20/69* (2022.01)
  *H04N 23/56* (2023.01)
  *H04N 23/698* (2023.01)

(52) U.S. Cl.
  CPC .......... *G03H 1/0005* (2013.01); *G06V 10/16* (2022.01); *G06V 10/82* (2022.01); *G06V 20/69* (2022.01); *G06V 20/698* (2022.01); *H04N 23/56* (2023.01); *H04N 23/698* (2023.01); *G03H 2001/005* (2013.01)

(58) Field of Classification Search
  CPC .... G03H 1/0443; G03H 1/0866; G06V 10/16; G06V 10/82; G06V 20/69; G06V 20/698; H04N 23/56; H04N 23/698; G06F 18/24143; G06N 3/045; G06N 3/084; G06N 3/048
  See application file for complete search history.

(56) References Cited

U.S. PATENT DOCUMENTS

| | | | |
|---|---|---|---|
| 11,262,286 B2 | 3/2022 | Ozcan et al. | |
| 11,347,000 B2 | 5/2022 | Ozcan et al. | |
| 2004/0252875 A1 | 12/2004 | Crandall et al. | |
| 2016/0289729 A1* | 10/2016 | Richards | G01N 1/38 |
| 2016/0327473 A1 | 11/2016 | Ozcan et al. | |
| 2018/0089828 A1* | 3/2018 | Wiles | G01N 21/27 |
| 2018/0196193 A1 | 7/2018 | Ozcan et al. | |
| 2018/0373921 A1 | 12/2018 | Di Carlo et al. | |
| 2019/0011882 A1* | 1/2019 | Gusyatin | G01N 15/1433 |
| 2019/0251330 A1 | 8/2019 | Cotte et al. | |
| 2019/0294108 A1 | 9/2019 | Ozcan et al. | |
| 2019/0316172 A1 | 10/2019 | Ozcan et al. | |
| 2019/0346369 A1 | 11/2019 | Ozcan et al. | |
| 2020/0103328 A1 | 4/2020 | Ozcan et al. | |
| 2020/0310100 A1 | 10/2020 | Ozcan et al. | |
| 2020/0340901 A1 | 10/2020 | Ozcan et al. | |
| 2021/0043331 A1 | 2/2021 | Ozcan et al. | |
| 2021/0209337 A1 | 7/2021 | Ozcan et al. | |
| 2021/0264214 A1 | 8/2021 | Ozcan et al. | |
| 2021/0374381 A1* | 12/2021 | Ozcan | G06V 30/19173 |
| 2022/0066390 A1* | 3/2022 | Gusyatin | G06V 10/82 |
| 2022/0114711 A1 | 4/2022 | Ozcan et al. | |
| 2022/0122313 A1 | 4/2022 | Ozcan et al. | |
| 2022/0206434 A1 | 6/2022 | Ozcan et al. | |
| 2024/0282126 A1* | 8/2024 | Debski | C12Q 1/18 |

FOREIGN PATENT DOCUMENTS

| | | | |
|---|---|---|---|
| WO | WO 2015/08820 | 7/2015 | |
| WO | WO 2016/205736 | 12/2016 | |
| WO | WO 2017/196885 | 11/2017 | |
| WO | WO-2017196885 A1 * | 11/2017 | ......... G02B 21/0008 |
| WO | WO 2018/057972 | 3/2018 | |
| WO | WO 2018/102346 | 6/2018 | |
| WO | WO 2018/136474 | 7/2018 | |
| WO | WO 2019/103909 | 5/2019 | |
| WO | WO 2019/236569 | 12/2019 | |
| WO | WO 2020/082029 | 4/2020 | |
| WO | WO 2020/082030 | 4/2020 | |
| WO | WO 2020/242993 | 12/2020 | |
| WO | WO 2021/133847 | 7/2021 | |
| WO | WO 2021/154876 | 8/2021 | |
| WO | WO 2021/188839 | 9/2021 | |

OTHER PUBLICATIONS

PCT International Preliminary Report on Patentability (Chapter I of the Patent Cooperation Treaty) for PCT/US2021/015321, Applicant: The Regents of the University of California, Form PCT/ISA/237, dated Aug. 11, 2022 (11 pages).
Maria Peñil Cobo et al., Visualizing Bacterial Colony Morphologies Using Time-Lapse Imaging Chamber Mocha, J Bacteriol 200:e00413-17, https://doi.org/10.1128/JB.00413-17 (Jan. 2018).
Colilert 18 (2019) IDEXX US. https://www.idexx.com/en/water/water-products-services/colilert-18/.
Alon Greenbaum et al., Wide-field computational imaging of pathology slides using lens-free on-chip microscopy, www.ScienceTranslationalMedicine.org, Dec. 17, 2014, vol. 6, Issue 267, 267ra175.
Alon Greenbaum et al., Increased space-bandwidth product in pixel super-resolved lensfree on-chip microscopy, Scientific Reports, 3:1717, DOI:10.1038/srep01717.
Gao Huang et al., Densely Connected Convolutional Networks, arXiv:1608.06993 [cs] (2016).
Janine R. Hutchison et al., Consistent production of chlorine-stressed bacteria from non-chlorinated secondary sewage effluents for use in the U.S. Environmental Protection Agency Alternate Test Procedure protocol, Journal of Microbiological Methods 163 (2019) 105651.
Serhan O. Isikman et al., Lens-free optical tomographic microscope with a large imaging volume on a chip, PNAS, May 3, 2011, vol. 108, No. 18, 7296-7301.
Diederik P. Kingma et al., Adam: A Method for Stochastic Optimization, arXiv:1412.6980v9 [cs.LG] Jan. 30, 2017.
Roanna London et al., An Automated System for Rapid Non-Destructive Enumeration of Growing Microbes, PLoS ONE 5(1): e8609. doi:10.1371/journal.pone.0008609.
Stephan Preibisch et al., Globally optimal stitching of tiled 3D microscopic image acquisitions, Bioinformatics, 25, 1463-1465 (2009).
Zhaofan Qiu et al., Learning Spatio-Temporal Representation with Pseudo-3D Residual Networks, arXiv:1711.10305v1 [cs.CV] Nov. 28, 2017.
US EPA. Analytical Methods Approved for Compliance Monitoring under the Long Term 2 Enhanced Surface Water Treatment Rule. (2017), (12 pages).
Hongda Wang et al., Computational out-of-focus imaging increases the space-bandwidth product in lens-based coherent microscopy, Optica, vol. 3, No. 12, Dec. 2016, 1422-1429.
Yibo Zhang et al., Edge sparsity criterion for robust holographic autofocusing, Optics Letters, vol. 42, No. 19, Oct. 1, 2017, 3824-3827.
Yibo Zhang et al., Motility-based label-free detection of parasites in bodily fluids using holographic speckle analysis and deep learning, Light: Science & Applications (2018) 7:108.
Maylis Chapetais-Baron et al., Colony analysis and deep learning uncover 5-hydroxyindole as an inhibitor of gliding motility and iridescence in Cellulophaga lytica, Microbiology, vol. 164(3), Mar. 1, 2018, DOI:10.1099/mic.0.000617.

(56) References Cited

OTHER PUBLICATIONS

PCT International Search Report for PCT/US2021/015321, Applicant: The Regents of the University of California, Form PCT/ISA/210 and 220, dated Apr. 7, 2021 (4 pages).
PCT Written Opinion of the International Search Authority for PCT/US2021/015321, Applicant: The Regents of the University of California, Form PCT/ISA/237, dated Apr. 7, 2021 (9 pages).

* cited by examiner

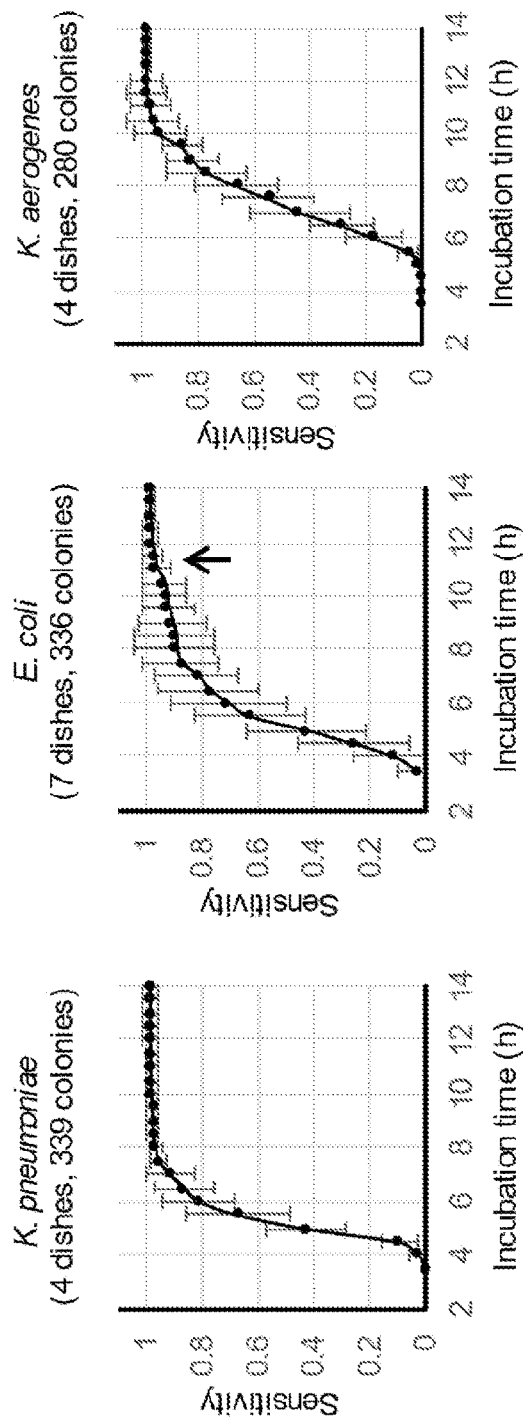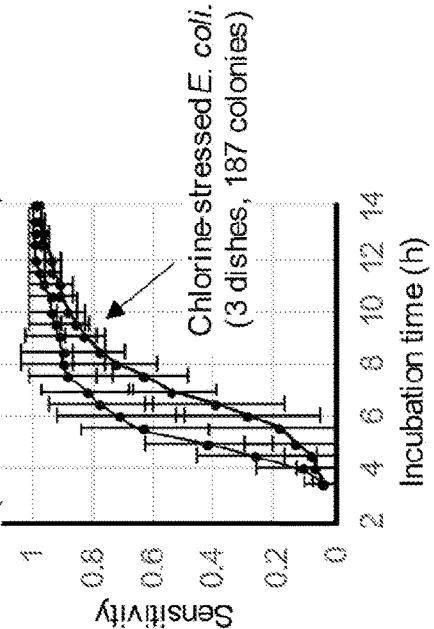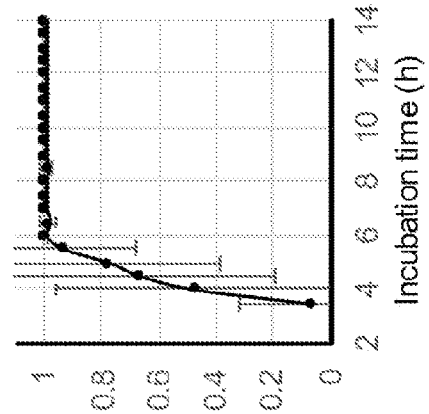

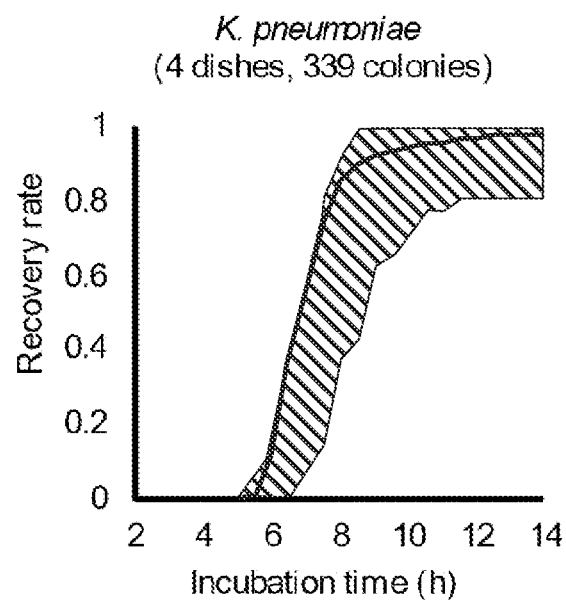
FIG. 6A
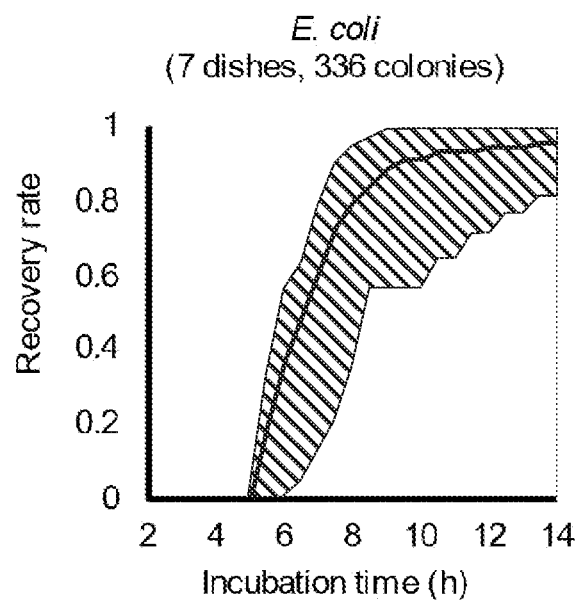
FIG. 6B
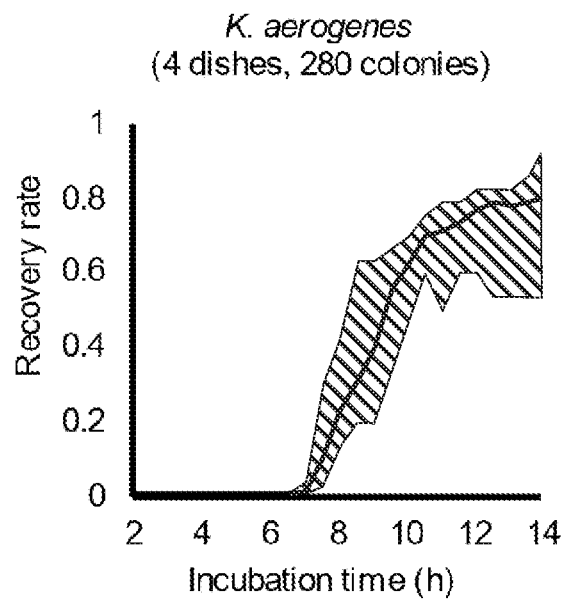
FIG. 6C
| Predicted / Actual | E. coli | K. aerogenes | K. pneumoniae |
|---|---|---|---|
| E. coli | 0.9723 | 0.0123 | 0.0154 |
| K. aerogenes | 0.0703 | 0.8398 | 0.0898 |
| K. pneumoniae | 0.0000 | 0.0150 | 0.9850 |
FIG. 6D

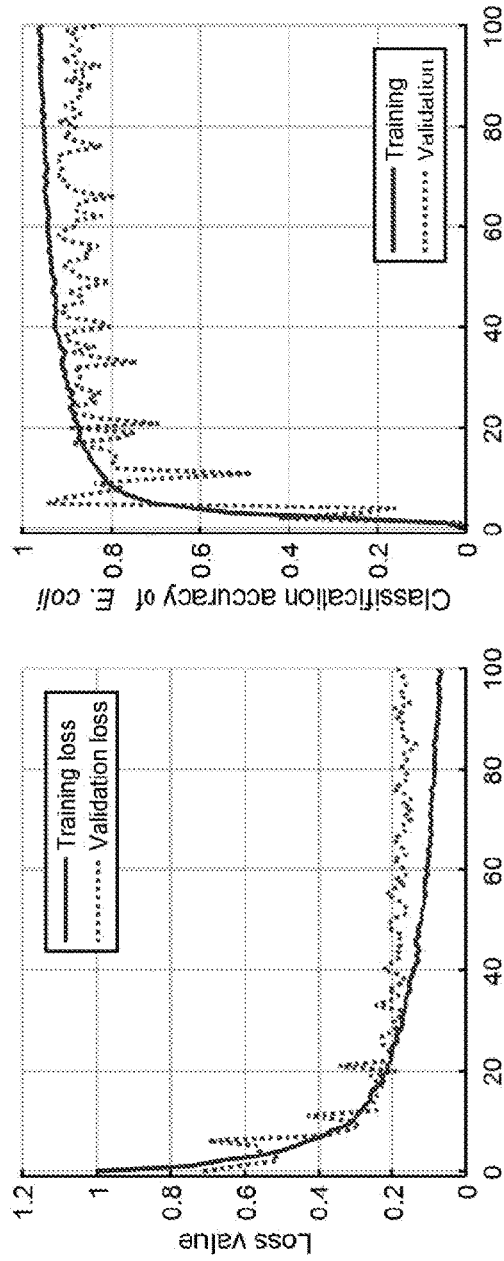
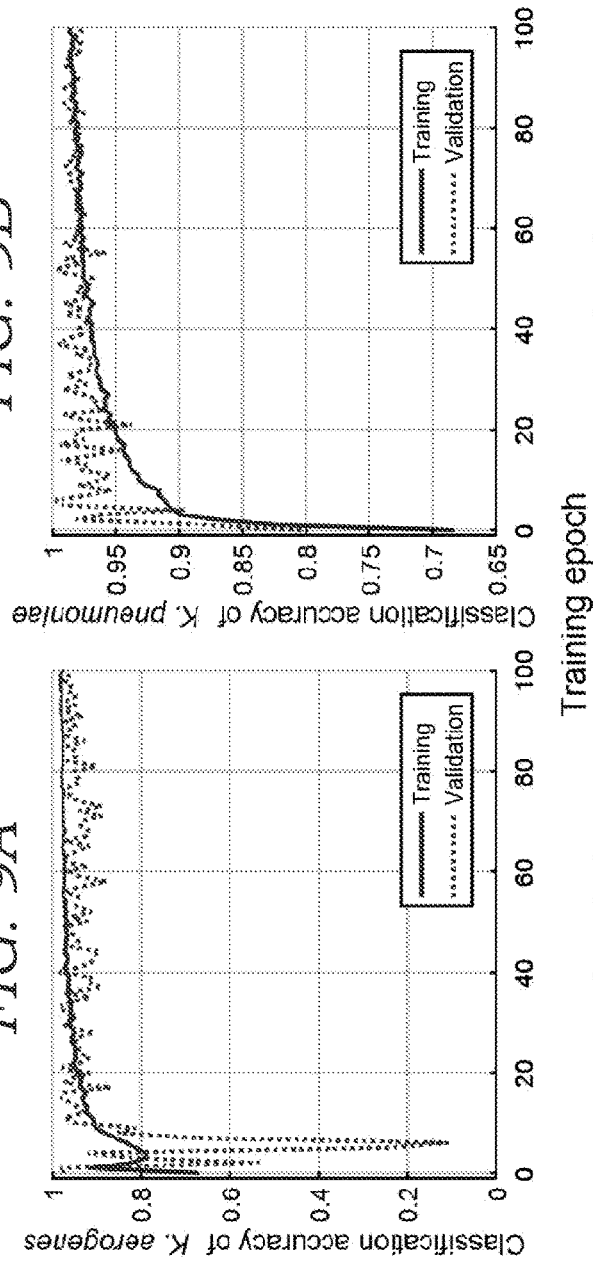
FIG. 9A  FIG. 9B  FIG. 9C  FIG. 9D

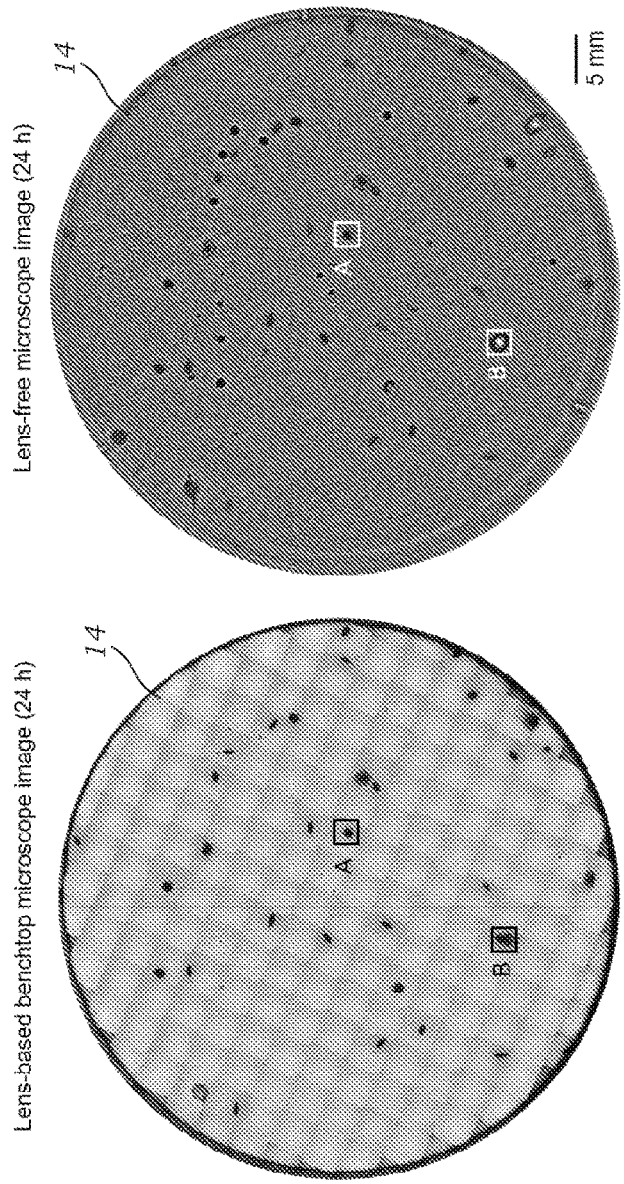
FIG. 13A
FIG. 13B
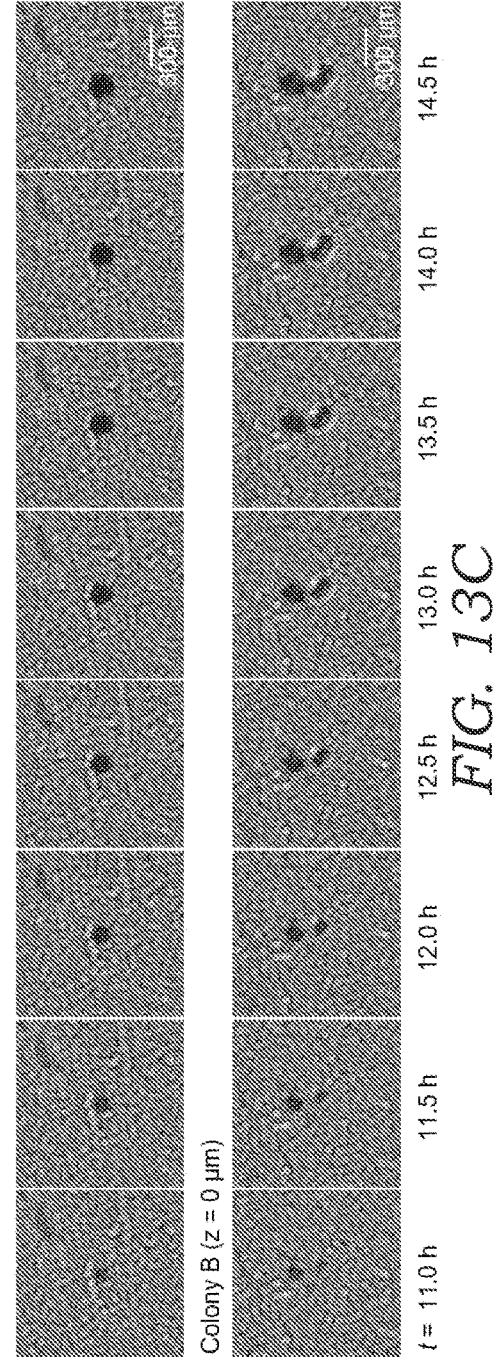
FIG. 13C

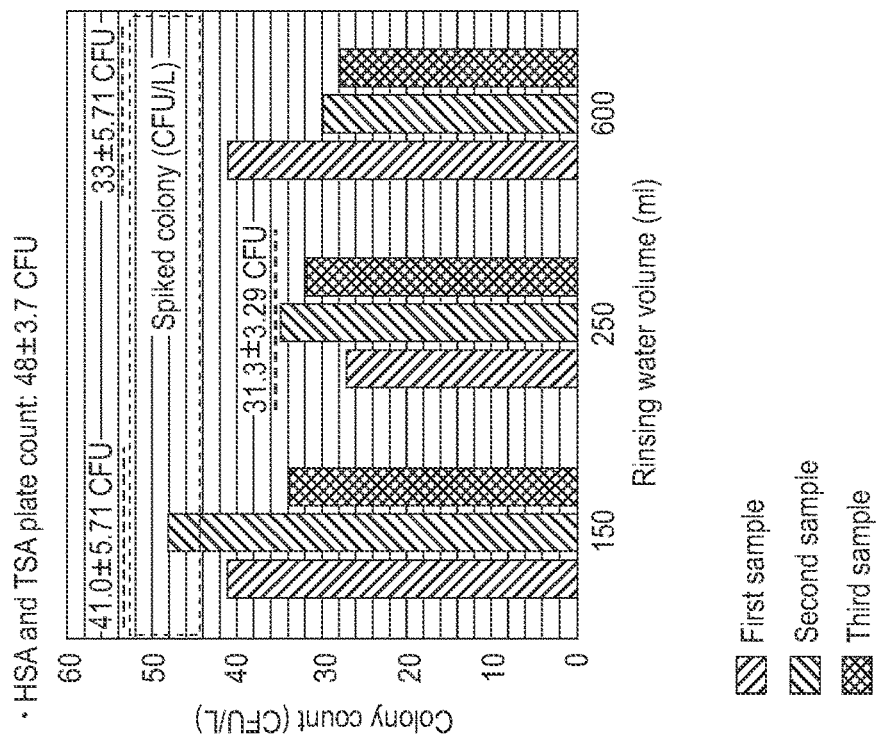
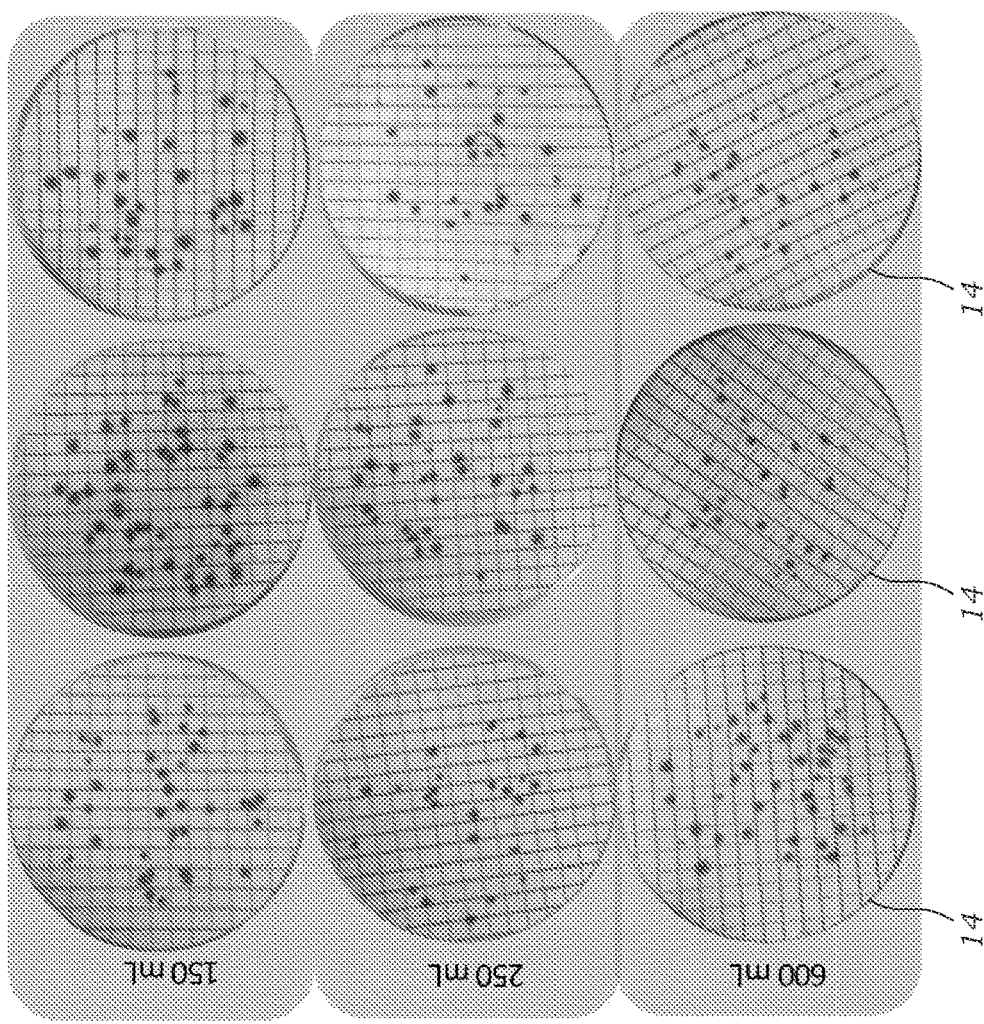
FIG. 14

Conditions for transfer time:

A. 5 min
B. 5 min + Continuous pressure (weight = 30 g)
C. 5 min + Continuous pressure (weight = 120 g)
D. 10 min
E. 15 min
F. 20 min

SYSTEMS AND METHODS FOR THE EARLY DETECTION AND CLASSIFICATION OF LIVE MICROORGANISMS USING TIME-LAPSE COHERENT IMAGING AND DEEP LEARNING

RELATED APPLICATION

This Application is a U.S. National Stage filing under 35 U.S.C. § 371 of International Application No. PCT/US2021/015321, filed on Jan. 27, 2021, which claims priority to U.S. Provisional Patent Application No. 62/966,965 filed on Jan. 28, 2020, which are hereby incorporated by reference. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under Grant Number W911NF-17-1-0161, awarded by the U.S. Army, Army Research Office. The government has certain rights in the invention.

TECHNICAL FIELD

The technical field generally relates to early screening and detection methods for the detection and/or identification of live microorganisms such as cells (prokaryotic or eukaryotic), viruses, fungi, bacteria, yeast, and multi-cellular organisms. More particularly, the technical field relates to systems and methods that periodically captures coherent microscopy images of bacterial growth on a growth plate and automatically analyzes these time-lapsed holograms using multiple deep neural networks for the rapid detection and/or classification of the corresponding microorganism species.

BACKGROUND

Rapid and accurate identification of live microorganisms is of great importance for a wide range of applications, including drug discovery screening assays, clinical diagnoses, microbiome studies, and food and water safety. Waterborne diseases, for example, affect more than 2 billion people worldwide, causing substantial economic burden; for example, treatment of waterborne diseases costs more than $2 billion annually in the United States (US) alone, with 90 million cases recorded per year. Among waterborne pathogen-related problems, one of the most common public health concerns is the presence of total coliform bacteria and *Escherichia coli* (*E. coli*) in drinking water, which indicates fecal contamination. Analytical methods used to detect *E. coli* and total coliforms are based on culturing the obtained samples on solid agar plates (e.g., the US Environmental Protection Agency (EPA) 1103.1 and EPA 1604 methods) or in liquid media (e.g., Colilert® test available from IDEXX Laboratories, Inc.), followed by visual recognition and counting by an expert, as described in the EPA guidelines. While the use of liquid growth media for the detection of fecal coliform bacteria provides high sensitivity and specificity, it requires at least 18 hours for the final read-out. The use of solid agar plates is a relatively more cost-effective method and provides flexibility for the volume of the sample to be analyzed, which can vary from 100 mL to several liters by using a membrane filtration technique to enhance sensitivity. However, this traditional culture-based detection method requires the colonies to grow to a certain macroscopic size for visibility, which often takes 24 to 48 hours in the case of bacterial samples. Alternatively, molecular detection methods based on e.g., the amplification of nucleic acids, can reduce the assay time to a few hours, but they generally lack the sensitivity for detecting bacteria at very low concentrations, e.g., one (1) colony-forming unit (CFU) per 100-1000 mL, and are not capable of differentiating between live and dead microorganisms. Furthermore, there is no EPA-approved nucleic acid-based analytical method for detecting coliforms in water samples.

All in all, there is a strong and urgent need for an automated method that can achieve rapid and high-throughput colony detection with high sensitivity (routinely achieving e.g., one (1) CFU per 100-1000 mL in less than 12 hours; to provide a powerful alternative to the currently available EPA-approved gold-standard analytical methods that: (1) are slow, taking ~24-48 hours to complete, and (2) require experts to read and quantify samples. To address this important need, various other approaches have been investigated for the detection of total coliform bacteria and *E. coli* in water samples, including solid phase cytometry, droplet based micro-optical lens arrays, fluorimetry, luminometry, and fluorescence microscopy. Despite the fact that these methods provide high sensitivity and some time savings, they cannot handle large sample sizes (e.g., ≥100 mL) or cannot perform automated classification of bacterial colonies.

SUMMARY

In one embodiment, a highly-sensitive and high-throughput system for the early detection and classification of live microorganisms and colony growth is disclosed that uses a time-lapse coherent imaging system along with, in some embodiments, two different deep neural networks (DNNs) for the detection and/or characterization or analysis of the detected microorganisms. The first DNN is used to detect microorganism (e.g., bacteria) growth as early as possible while the second DNN is used to classify the type of growing microorganisms, based on the spatio-temporal features obtained from the coherent images of an incubated agar-plate. In other embodiments, a single trained deep neural network that combines the functionalities of the detection and characterization of the two separate DNNs discussed above may also be used.

In this live microorganism detection system, which is preferably integrated with an incubator, lens-free holographic images of the growth plate (e.g., agar plate) sample are captured by a monochromatic complementary metal—oxide—semiconductor (CMOS) image sensor that is mounted on a translational stage. The system rapidly scans the entire area of two separate agar plates (— 56.52 cm$^2$) every 30 minutes, and utilizes these time-resolved holographic images for accurate detection, classification, and counting of the growing colonies as early as possible. This unique system enables high-throughput periodic monitoring of an incubated sample by scanning a 60-mm diameter agar-plate in 87 seconds with an image resolution of <4 μm. The system continuously calculates differential images of the sample of interest for the early and accurate detection of bacterial growth. The spatio-temporal features of each non-static object/feature on the plate are continuously analyzed using deep learning to yield the count of microorganism growth, and to automatically identify the type(s) of microorganism growing on different parts of the growth plate.

The efficacy of this platform was demonstrated by performing early detection and classification of three types of bacteria, i.e., *E. coli, Klebsiella aerogenes* (*K. aerogenes*), and *Klebsiella pneumoniae* (*K. pneumoniae*), and achieved a limit of detection (LOD) of ~1 CFU/L in <9 hours of total test time. See FIGS. 4A-4B. Moreover, a detection time savings of more than 12 hours was achieved as compared to the gold-standard EPA methods, which usually require at least 24 hours to obtain a result. Growth statistics of these three different species were also quantified and a detailed growth analysis of each type of bacteria over time is provided. The detection and classification neural networks were built, trained and validated with 16,000 individual colonies resulting from 71 independent experiments and were blindly tested with 965 individual colonies collected from 15 independent experiments that were never used in the training phase. In the blind testing, the trained neural network models demonstrated 80% detection sensitivity within 6-9 hours, 90% detection sensitivity within 7-10 hours, and >95% detection sensitivity within 12 hours, while maintaining ~99.2-100% precision at any time point after 7 hours, also achieving correct identification of 80% of all three the species within 7.6-12 hours. In terms of species-specific accuracy of the classification network, within 12 hours of incubation the system achieved ~97.2%, ~84.0%, and ~98.5% classification accuracy for *E. coli, K. aerogenes*, and *K. pneumoniae*, respectively. These results confirm the transformative potential of the system, which not only enables highly sensitive, rapid and cost-effective detection of live bacteria (with a cost of $0.6 per test or lower), but also provides a powerful and versatile tool for microbiology research.

In one embodiment, a system for the early detection and classification of live microorganisms in a sample using time-lapse imaging includes a partially-coherent light or fully coherent light source. The system includes an incubator configured to hold one or more growth plates therein containing the sample. The one or more growth plates containing the sample are disposed along an optical axis from the light source. A translation stage is part of the system and is mechanically coupled to at least one image sensor and/or the one or more growth plates, the translation stage configured to move the at least one image sensor and/or the one or more growth plates along one or more dimensions to capture holographic images of microorganisms on the one or more growth plates. The system includes control circuitry configured to drive the translation stage. Image processing software is executed using a computing device and processes and analyzes time-lapse holographic images of the microorganisms on the one or more growth plates. The computing device is configured to receive the captured time-lapse holographic images of the microorganisms on the one or more growth plates and contains or executes image processing software configured to detect candidate microorganism colonies in the time-lapse holographic images or reconstructed time-lapse images thereof based on differential image analysis. The computing device further includes a first trained deep neural network configured to detect true microorganism colonies from non-microorganism objects and a second trained deep neural network that receives as an input at least one time-lapsed holographic image or reconstructed image and/or at least one digitally processed time-lapsed image of the detected true microorganism colonies (i.e., from the first trained deep neural network) and outputs a species associated with each one of the detected true microorganism colonies.

In another embodiment, a method of using the above-described device includes placing one or more growth plates containing the sample in the incubator and illuminating the one or more growth plates with the light source. Periodically, the at least one image sensor and/or the one or more growth plates are then scanned with the translation stage to obtain a plurality of time-lapsed holographic images of the one or more growth plates. The method further includes processing the time-lapsed holographic images or reconstructed images thereof of the one or more growth plates with image processing software executed on a computing device, the image processing software configured to detect candidate microorganism colonies in the time-lapse holographic images or reconstructed images thereof based on differential image analysis and further including a first trained deep neural network configured to detect true microorganism colonies from non-microorganism objects and a second trained deep neural network that receives as an input at least one time-lapsed holographic image or reconstructed image thereof and/or at least one digitally processed time-lapsed image of the true microorganism colonies and outputs a species associated with each one of the detected true microorganism colonies.

In another embodiment, a method of detecting and classifying live microorganisms using time-lapse imaging includes loading one or more growth plates containing a sample into an incubator and illuminating the one or more growth plates with a partially-coherent or fully coherent light source. Periodically, the translation stage is used to periodically scan the at least one image sensor and/or the one or more growth plates along one or more dimensions with the translation stage to capture holographic images of microorganisms on the one or more growth plates. A plurality of image tiles of the one or more growth plates are captured with the image sensor for each periodic scanning operation. The plurality of image tiles from the periodic scans are digitally stitched together to generate a full field-of-view (FOV) time-lapsed images of the one or more growth plates with image processing software. The full FOV time-lapsed images of the one or more growth plates obtained over different time periods are registered with one another using the image processing software. Candidate microorganism colonies are detected in the registered time-lapse images with the image processing software based on differential analysis in the registered time-lapse images. A first trained deep neural network is executed by a computing device that is configured to detect true microorganism colonies from non-microorganism objects from the candidate microorganism colonies. A second trained deep neural network is executed by the computing device that receives as an input at least one time-lapsed image and/or at least one digitally processed time-lapsed image of the true microorganism colonies and outputs a species associated with each one of the detected true microorganism colonies.

In another embodiment, a method of detecting and classifying live microorganisms using time-lapse imaging includes loading one or more growth plates containing a sample into an incubator and illuminating the one or more growth plates with a partially-coherent or fully coherent light source. Time-lapse holographic images of microorganisms on the one or more growth plates are captured. The time-lapsed holographic images are reconstructed into reconstructed time-lapse images and candidate microorganism colonies are detected in the reconstructed time-lapse images with the image processing software based on differential image analysis. A first trained deep neural network is executed using a computing device and configured to detect true microorganism colonies from non-microorganism objects in the candidate microorganism colonies and a second trained deep neural network is executed that receives as an input at least one reconstructed time-lapsed image and/or at least one digitally processed time-lapsed image and outputs a species associated with each one of the detected true microorganism colonies.

In another embodiment, a system for the early detection and classification of live microorganisms using time-lapse imaging includes a partially-coherent or fully coherent light source. The system includes an incubator configured to hold one or more growth plates therein or thereon containing a sample with the one or more growth plates disposed along an optical axis from the light source. A translation stage is provided that is mechanically coupled to at least one image sensor. The one or more growth plates may be mechanically coupled to the translation stage instead of or in addition to the at least one image sensor. The translation stage is configured to move the at least one image sensor and/or the one or more growth plates along one or more dimensions to capture holographic images of microorganisms on the one or more growth plates. Control circuitry is provided and is configured to drive the translation stage. At least one computing device is provided and configured to receive captured time-lapse images of the microorganisms on the one or more growth plates and includes image processing software configured to detect candidate microorganism colonies in the time-lapse holographic images or reconstructions thereof based on differential image analysis in the time-lapse images and further including a trained deep neural network configured to detect true microorganism colonies from non-microorganism objects as well as output a species associated with each of the detected true microorganism colonies In another embodiment, a method of detecting and classifying live microorganisms using time-lapse imaging includes loading one or more growth plates containing a sample onto or within an incubator and illuminating the one or more growth plates with a partially-coherent or fully coherent light source. Time-lapse holographic images of microorganisms on the one or more growth plates are captured. Candidate microorganism colonies are detected in the time-lapse holographic images or reconstructions thereof with the image processing software based on differential image analysis. A trained deep neural network is executed using the computing device that is configured to detect true microorganism colonies from non-microorganism objects in the candidate microorganism colonies as well as output a species associated with each one of the detected true microorganism colonies.

BRIEF DESCRIPTION OF THE DRAWINGS

FIG. 3A shows the bacterial sample preparation workflow according to one embodiment.

FIG. 3B illustrates the operations of the image and data processing algorithms for automated detection of growing colonies and classification of their species. The scale bars for the holographic images of the growing colonies (*E. coli* and *K. aerogenes*) and a static particle (dust) are 100 μm.

FIGS. 5A-5E illustrate graphs of sensitivity and precision of growing colony detection using the trained neural network for different strains of bacteria. FIG. 5A: *K. pneumoniae*, FIG. 5B: *E. coli*, and FIG. 5C: *K. aerogenes*. FIG. 5D illustrates a graph of the precision of growing colony detection using the trained neural network for all three species. The arrow in FIG. 5B indicates the time for late "wake-up" behavior for some of the *E. coli* colonies. FIG. 5E illustrates a graph characterizing the growth speed of chlorine-stressed *E. coli* using the system. There is a h delay of colony formation for chlorine-stressed *E. coli* (the lower curve) compared to the unstressed *E. coli* strain (the upper curve).

FIGS. 6A-6C illustrate the classification performance of the trained neural network for *K. pneumoniae* (FIG. 6A), *E. coli* (FIG. 6B), and *K. aerogenes* (FIG. 6C) colonies. The shaded area in each curve represents the highest and lowest recovery rates found in all the corresponding experiments at each time point.

FIG. 6D illustrates the blind testing confusion matrix of classifying all the colonies that were sent to the trained neural network after 12 hours of incubation. A diagonal entry of 1.0 means 100% classification accuracy for that species. The number of colonies that were tested by the classification network were as follows: 325 (*E. coli*), 334 (*K. pneumoniae*), and 256 (*K. aerogenes*).

FIG. 7A is the CFU count from the system is plotted against the CFU/L counts of the spiked samples, calculated independently using the Colilert® 18 method after 18 hours of incubation. CFU counts acquired with the platform at different time points are colored from blue to yellow, which corresponds to 5 to 14.5 hours of total test time, including the signal amplification step that involves liquid culture media (5 h). Without signal amplification (FIG. 7B), the LOD is decreased due the low transfer rate from filter membrane to the agar surface. As a control experiment (FIG. 7C), 3 agar plates were prepared and imaged which show <1 CFU count from the setup throughout the test period from 5 h to 14.5 h. (FIG. 7D) The LOD of the system is ~11 CFU/L at 8.5 h and ~1 CFU/L at <9 h.

FIGS. 9A-9D illustrates training loss (FIG. 9A) and classification accuracy curves (FIGS. 9B-9D) of the neural network model for colony species classification.

(FIG. 12A) Raw hologram captured by the image sensor. (FIG. 12B) Digitally back-propagated hologram. (FIG. 12C) Zoomed-in region demonstrates a half-pitch resolution of ~3.5 µm.

FIGS. 13A-13C illustrate images of *E. coli* colonies grew at different depths within the 3D culture medium. Image (FIG. 13A) of the sample plate captured using a lens-based benchtop microscope after 24 hours of incubation and stitched by the microscope software. Image (FIG. 13B) of the sample plate captured using the lens-free microscope at 24 hours of incubation. Images (FIG. 13C) of 2 colonies (A and B) marked in (FIG. 13A) and (FIG. 13B) that grew at different depths, axially separated by ~2.17 mm.

FIG. 14 illustrates colony counts obtained for optimization of the amount of water used for washing the sample container. Plate images are also shown on the right.

DETAILED DESCRIPTION OF ILLUSTRATED EMBODIMENTS

Figure 1:
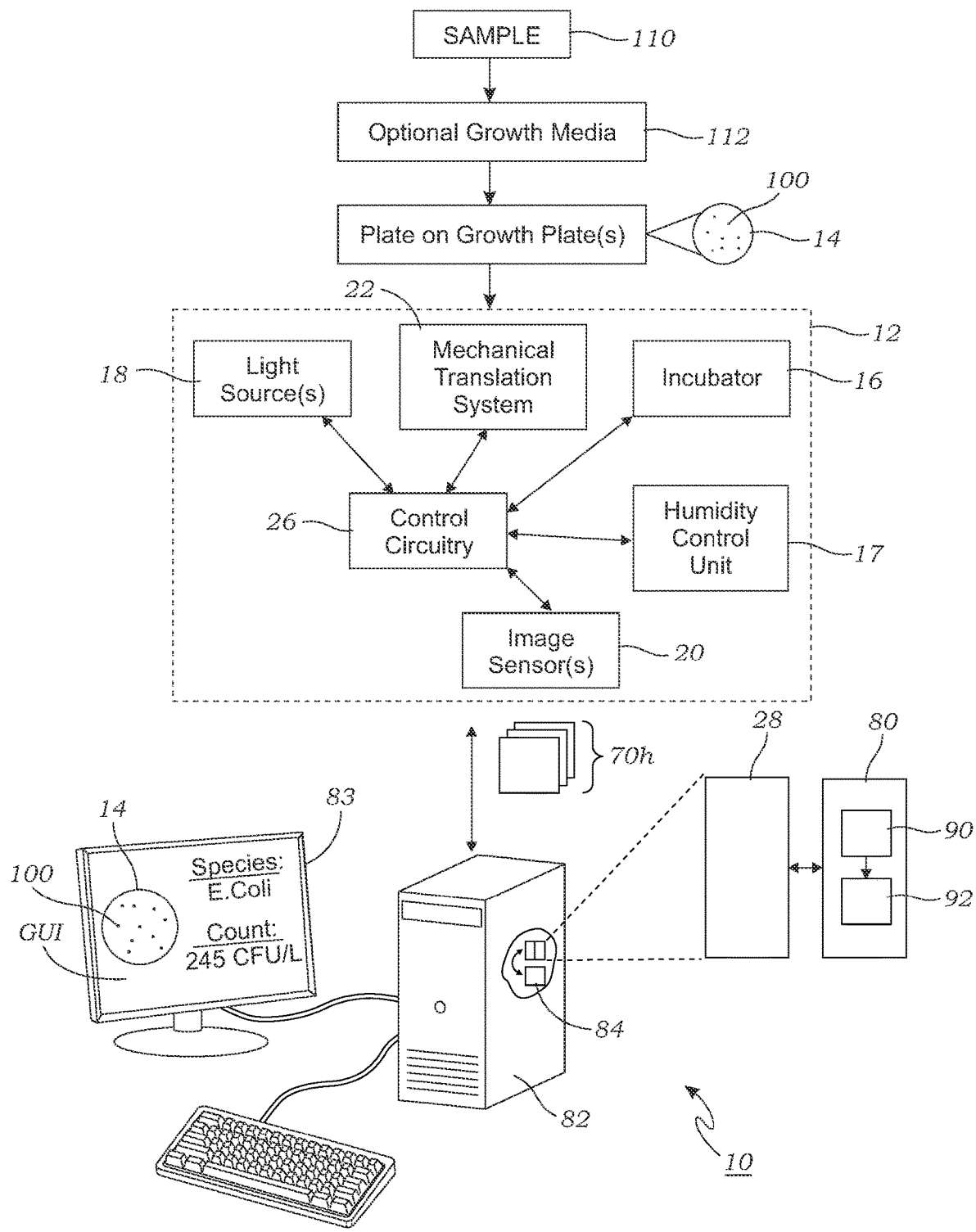
FIG. 1 schematically illustrates one embodiment of a system for the early detection and classification of live microorganisms using time-lapse coherent imaging and deep learning.

FIG. 1 illustrates a system 10 for the early detection and classification of live microorganisms 100 in a sample 110 using time-lapse coherent imaging and deep learning according to one embodiment. Microorganisms 100 include prokaryotic cells, eukaryotic cells (e.g., stem cells), fungi, bacteria, viruses, multi-cellular organisms (e.g., parasites) or clusters or films thereof. The system 10 includes a holographic imager device 12 (see also FIGS. 2A-2C) that is used to obtain time-lapsed images 70h of microorganism growth occurring on one or more growth plates 14 (e.g., Petri dish that contains agar as a solid growth medium plus nutrients used to culture microorganisms or other growth medium(s) appropriate for the type of microorganism 100). The holographic imager device 12 includes an incubator 16 to heat the one or more growth plates 14 and maintain the temperature at optimal setpoint temperature(s) or temperature range(s) for microorganism growth. The incubator 16 may include, in one embodiment, an optically transparent plate or substrate that contains heating elements therein that are used to adjust the temperature of the one or more growth plates 14. In the experimental setup described herein, an optically transparent region (that functioned as the incubator 16) was provided in an opaque frame 62 or support and held a single growth plate 14. In this regard, the one or more growth plates 14 are in thermal contact with the incubator 16. The incubator 16 may also include a fully or partially enclosed housing that contains the one or more growth plates 14. The holographic imager device 12 may also include one or more optional humidity control units 17 which are used to maintain the one or more growth plates 14 at a setpoint humidity level or range. The humidity control unit(s) 17 may be integrated with the incubator 16 or a separate component. A series of time-lapsed holographic images 70h of the growth plates 14 (or other sample holder containing the microorganisms) is used to identify microorganism colony candidates based on differential images obtained over time. The differential images (images 70h obtained at different times) include images of growing microorganism colonies 102 but also includes non-microorganism objects such as water bubbles or surface movement of the agar itself, and other artifacts. Image processing software 80 executed on a computing device 82 having one or more processors 84 is used to back-propagate these holographic images 70h to at least one sample plane to create reconstructed images 70r. The back-propagated differential image 70d is made using a plurality of consecutive image frames of the reconstructed images 70r and is then processed to identify regions-of-interest therein that exhibit differences above an empirically established threshold (e.g., using intensity). These regions-of-interest are marked as colony candidates 260. However, some of these colony candidates 260 are not true microorganism colonies 102 but may represent non-living objects or artifacts such as bubbles, dust, and the like which need to be masked or excluded. As explained herein, a first trained deep neural network (DNN) 90 is used by the image processing software 80 to detect the actual microorganism colonies 102 and ignore the non-microorganism objects. Once the "true" microorganism colonies 102 are selected, one or more of the time-lapsed image(s) 70r and/or at least one digitally processed time-lapsed image (e.g., digitally processed images 70r showing differences, thresholded or filtered images) are sent to a second trained deep neural network (DNN) 92 that is used to classify the species of the microorganism(s) 100 that form the colony 102.

Referring to FIGS. 1 and 2A-2C, the system 10 is implemented with a holographic imager device 12 that includes a holographic imaging system that captures hologram images of growing microorganisms 100. A light source 18 (e.g., laser light) that is partially-coherent or fully coherent illuminates the microorganisms 100 on the one or more growth plates 14 (which are incubated using the incubator 16) and holographic images 70h of the microorganisms 100 are captured with at least one image sensor 20 (e.g., CMOS image sensor). The holographic imager device 12 may be placed inside a separate incubator 16 or the holographic imager device 12 may be integrated with the incubator 16. A mechanical translation system 22 is provided that includes a moveable stage 24 that is mechanically coupled to the at least one image sensor 20 and/or the one or more growth plates 14 to image or scan in at least one dimension over the surface of the growth plates 14. For example, the at least one image sensor 20 may be mounted on the moveable stage 24 that allows one to image over a region of the growth plates 14. In one preferred embodiment, the moveable stage 24 allows scanning all or a portion of the one or more growth plates 14 in two dimensions (e.g., x and y direction). In some embodiments, however, only a single dimensional scan is needed (e.g., x or y). In still other embodiments, scanning may be omitted entirely and the at least one image sensor 20 may be stationary. This may be the case if a lens or set of lenses is used to capture a large field of view of the one or more growth plates 14. Likewise, a larger sized image sensor 20 may obviate the need for the scanning operation.

Control circuitry 26 is provided that is used to control the mechanical translation system 22 (if used). The control circuitry 26 may also communicate with the computing device 82, for example, to receive movement instructions and/or send data using a controlling program 28 executed by the computing device 82. The control circuitry 26 may include one or more microprocessors or microcontrollers that are used to operate various subsystems and transfer data. The control circuitry 26 may also be used to control the setpoint temperature or temperature range of the incubator 16. The control circuitry 26 may also be used to control the setpoint humidity level or humidity range of the incubator 16. The incubator 16 is integrated into the system 10, in one preferred embodiment, and includes one or more heaters that are used to control the temperature of the one or more growth plates 14. One or more humidity control units 17 may also be present to control the humidity level of the incubator 16. Control circuitry 26 is provided to control actuation of the translation system 22, heating of the incubator 16, humidity of the incubator 16 (if applicable), light source 18, and the image sensor(s) 20. The system 10 includes at least one computing device 82 (e.g., personal computer, laptop, tablet PC, server, or the like) having one or more processors 84 therein which is used to execute image processing software 80 to process the images 70$h$, 70$r$, 70$d$ obtained from the image sensor(s) 20. In addition, the computing device 82 is able to control various aspects of the operation of the holographic imager device 12 using the control circuitry 26. For example, using a graphical user interface (GUI) viewable on a display 83, the user can control the operation of the translation system 22 and other aspects of the system 10 (e.g., periodicity or timing of image scans, image sensor 20 operation, temperature control of incubator 16, transfer of image files 70 from image sensor(s) to computing device 82, etc.). The GUI may also be used to display classified colonies 102, colony counts, and display a colony growth map 310 for viewing/interaction.

In one embodiment, image processing software 80 is used to digitally combine or stitch the image tiles together to generate an image of all or a larger region of the one or more growth plates 14 along with image registration, differential image analysis, and microorganism colony 102 selection. In addition, the computing device 82 executes the colony detection deep neural network 90 in the image processing software 80 which is used to identify the true microorganism colonies 102 from other non-microorganism artifacts (e.g., dust, bubbles, speckle, etc.). The computing device 82 also executes a separate classification deep neural network 92 in the image processing software 80 that classifies the particular species of microorganism 100 in the growing colonies 102. In an alternative embodiment, the functions of the first and second trained deep neural networks 90, 92 are combined into a single trained deep neural network (e.g., deep neural network 90). Multiple different species of colonies 102 may be identified in a single sample. In one particular embodiment, the system 10 enables the rapid detection of *Escherichia coli* and total coliform bacteria (i.e., *Klebsiella aerogenes* and *Klebsiella pneumoniae* subsp. *pneumoniae*) in water samples. This automated and cost-effective live microorganism detection system 10 is transformative for a wide range of applications in microbiology by significantly reducing the detection time, also automating the identification of microorganisms 100 in colonies 102, without labeling or the need for an expert.

To use the system 10, a sample 110 is obtained and optionally subject to a signal amplification operation where the sample is pre-incubated with a growth medium 112 (FIG. 1) for a period of time at elevated temperatures followed by filtration using, for example, a filter membrane. The sample 110 is a fluid and may include, for example, a water sample. The filter membrane is then placed in physical contact with one or more growth plates 14 (e.g., agar surface of growth plate 14) for a period of time under light pressure to transfer the microorganisms 100 (e.g., bacteria) to the agar growth medium in the growth plates 14 and then removed. The one or more growth plates 14 are then placed in the holographic imager device 12 (with the agar surface facing the image sensor(s)) 20 in/on the incubator 16. The growth plate(s) 14 with the sample 110 is then allowed to incubate for several hours and is periodically imaged by the moving image sensor(s) 20 and/or one or more growth plates 14 using the mechanical translation system 22. In some embodiments, a single growth plate 14 is imaged by the image sensor 20. In other embodiments, multiple growth plates 14 are imaged by the image sensor 20.

Figure 3A:
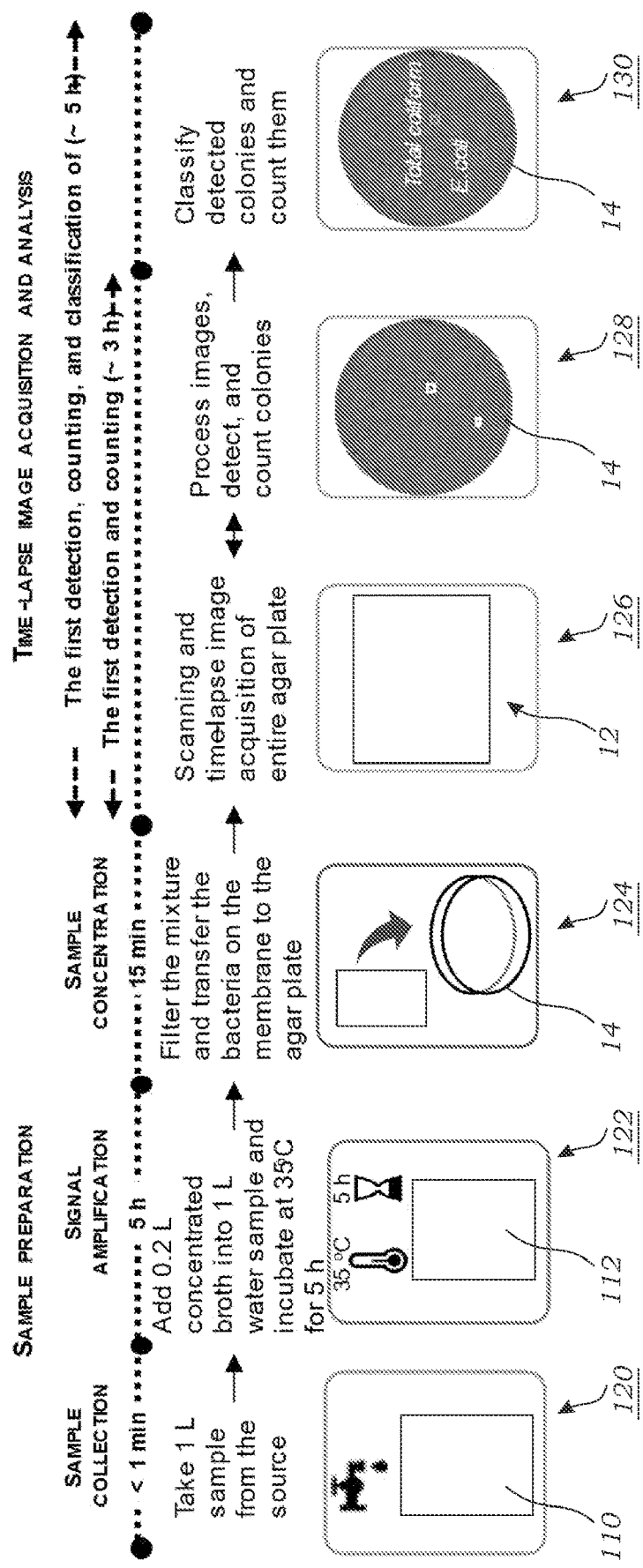
FIGS. 3A-3B schematically illustrates the workflow of the microorganism monitoring system.

In one particular embodiment, a method of detecting and classifying live microorganisms 100 using time-lapse imaging includes loading one or more growth plates 14 containing a sample 110 into or onto an incubator 16. FIG. 3A illustrates how a sample is collected and processed prior to loading into the one or more growth plates 14. For example, 1 L of sample (fluid) is taken from the source to be tested as seen in operation 120. Next, optional signal amplification is performed as seen in operation 122 as 0.2 L of concentrated growth media (e.g., broth) is added to the 1 L water sample and allowed to incubate at 35° C. for 5 hours. Next, as seen in operation 124, the mixture is then passed through a filter and the trapped bacteria or other microorganisms 100 are transferred to the solid media on the one or more growth plates 14.

The one or more growth plates 14 are then illuminated with a partially-coherent or fully coherent light source 18. The one or more growth plates 14 are scanned to obtain time-lapse images 70$h$ thereof using the holographic imager device 12 (operation 126). The images 70$h$ are then processed and true microorganism colonies 102 are detected and counted as seen in operation 128. Finally, the detected microorganism colonies 102 are then classified and/or counted as seen in operation 130.

Figure 2A:
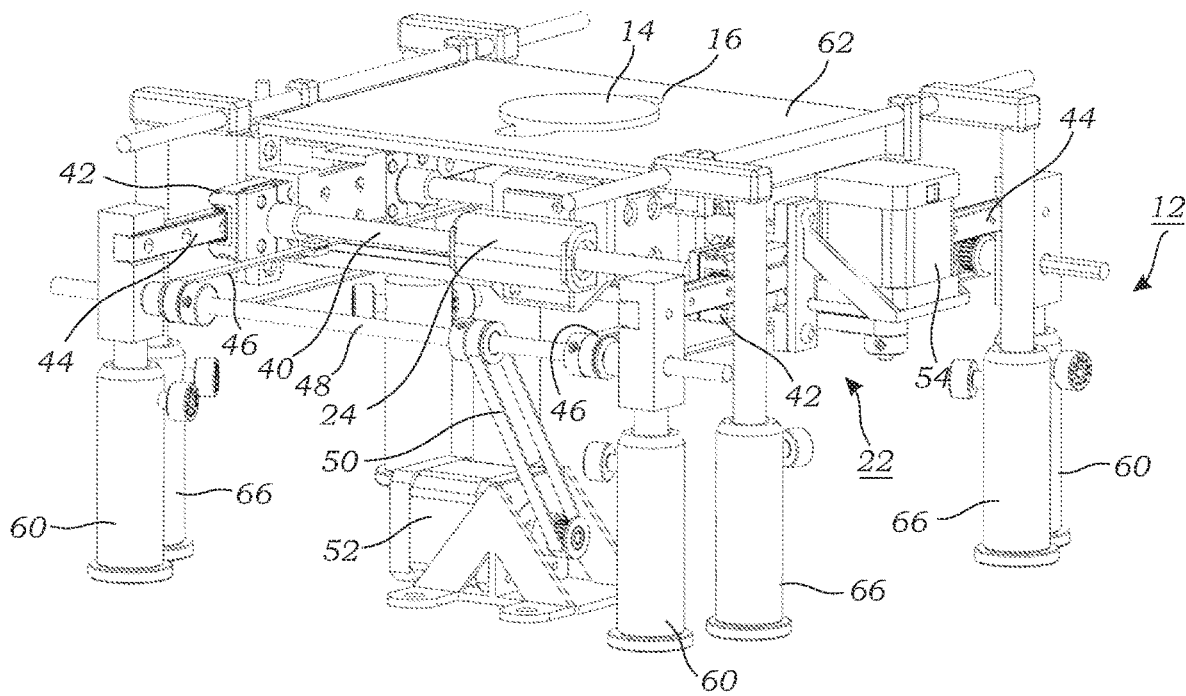
FIG. 2A illustrates a perspective view one embodiment of the high-throughput bacterial colony growth detection and classification system (excluding light source).
Figure 2B:
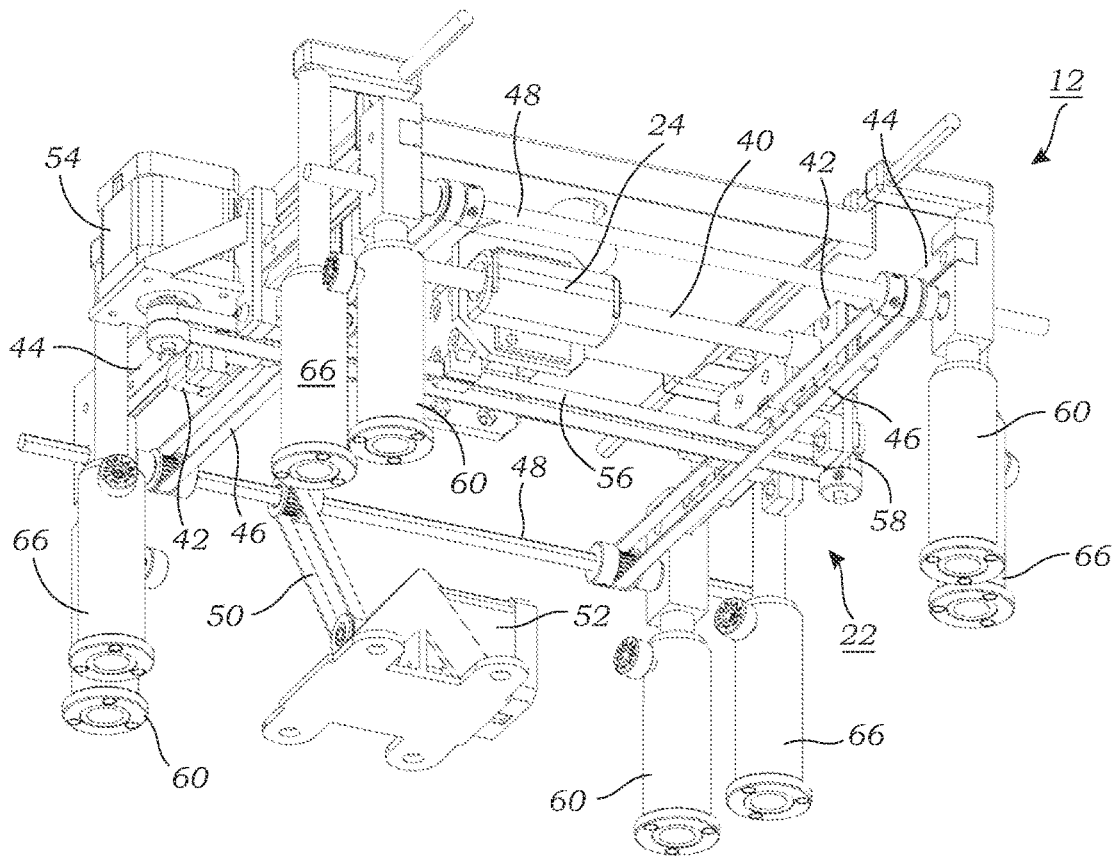
FIG. 2B illustrates another perspective view one embodiment of the high-throughput bacterial colony growth detection and classification system (excluding light source).
Figure 2C:
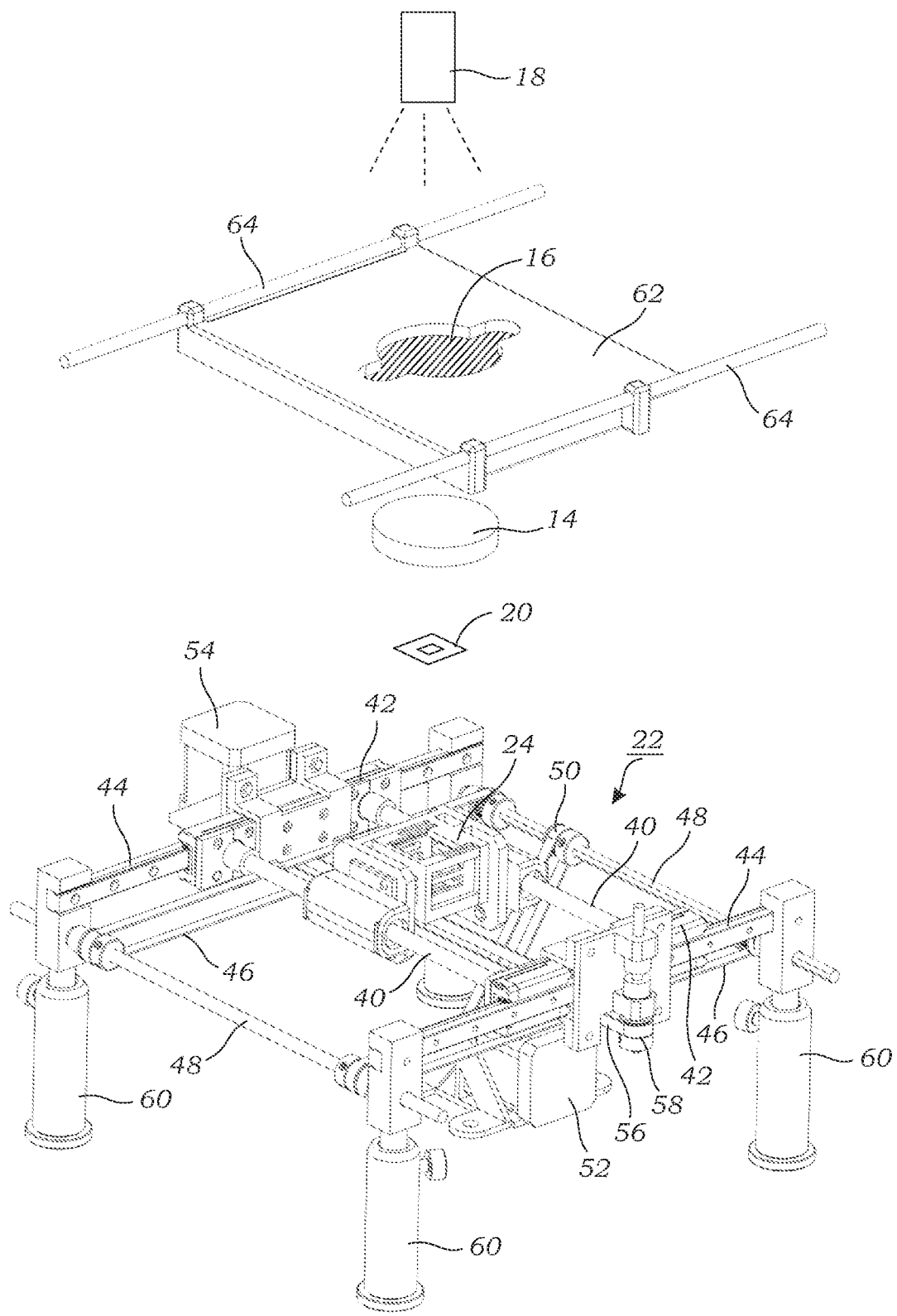
FIG. 2C illustrates an exploded view of the high-throughput bacterial colony growth detection and classification system including the light source.

FIGS. 2A-2C illustrate the holographic imager device 12 that was used in the experiments described herein. The holographic imager device 12 includes a mechanical translation system 22 that includes a moveable stage 24 that is mounted to a pair of linear bearing rods 40 using linear bearings (not shown). As best seen in FIG. 2B, the at least one image sensor 20 is carried by the moveable stage 24. The moveable stage is able to move in a first direction (e.g., x direction) along the linear bearing rods 40. The ends of the pairs of linear bearing rods 40 are secured to respective carriages 42 that are slidable along a pair of linear translation rails 44. The carriages 42 move in a second direction generally orthogonal to the first direction (e.g., y direction). In this way, the at least one image sensor 20 can be moved in two dimensions to image or scan different regions of the surface(s) of the one or more growth plates 14. FIG. 2C illustrates the light source 18 that emits illumination light onto the one or more growth plates 14. The carriages 42 are each secured to respective belts 46 that loop around respective pulley rods 48 at opposing ends. A drive belt 50 connected to a first motor 52 drives the pully rod 48 and thus imparts movement of the carriages 42 (and thus moveable stage 24) along the x direction. A second motor 54 is provided that drives a belt 56 that is secured to the moveable stage 24 and is looped around a pulley 58 located opposite the second motor 54.

The portion of the holographic imager device 12 that includes the mechanical translation system 22 is supported by four (4) separate feet 60 that support the pair of linear bearing rods 40 and the pair of linear translation rails 44. The incubator 16 is a separate portion of the holographic imager device 12 and includes a frame 62 with a recess for holding the one or more growth plates 14. The bottom of this recess includes the incubator 16 which, in one embodiment, is an optically transparent material that includes heating elements contained therein to heat the one or more growth plates 14. The frame 62 are held by a pair of rods 64 are connected to four (4) separate feet 66. The respective heights of the feet 60, 66 place the one or more growth plates 14 adjacent to the active (imaging) area of the at least one image sensor 20. In this embodiment, the one or more growth plates 14 is fixed in position (e.g., in the x, y, and z directions) while the at least one image sensor 20 is moveable in the x and/or y directions by actuation of the first motor 52 and second motor 54. The entire system 10 may sit atop a flat surface (e.g., benchtop) during operation.

Figure 3B:
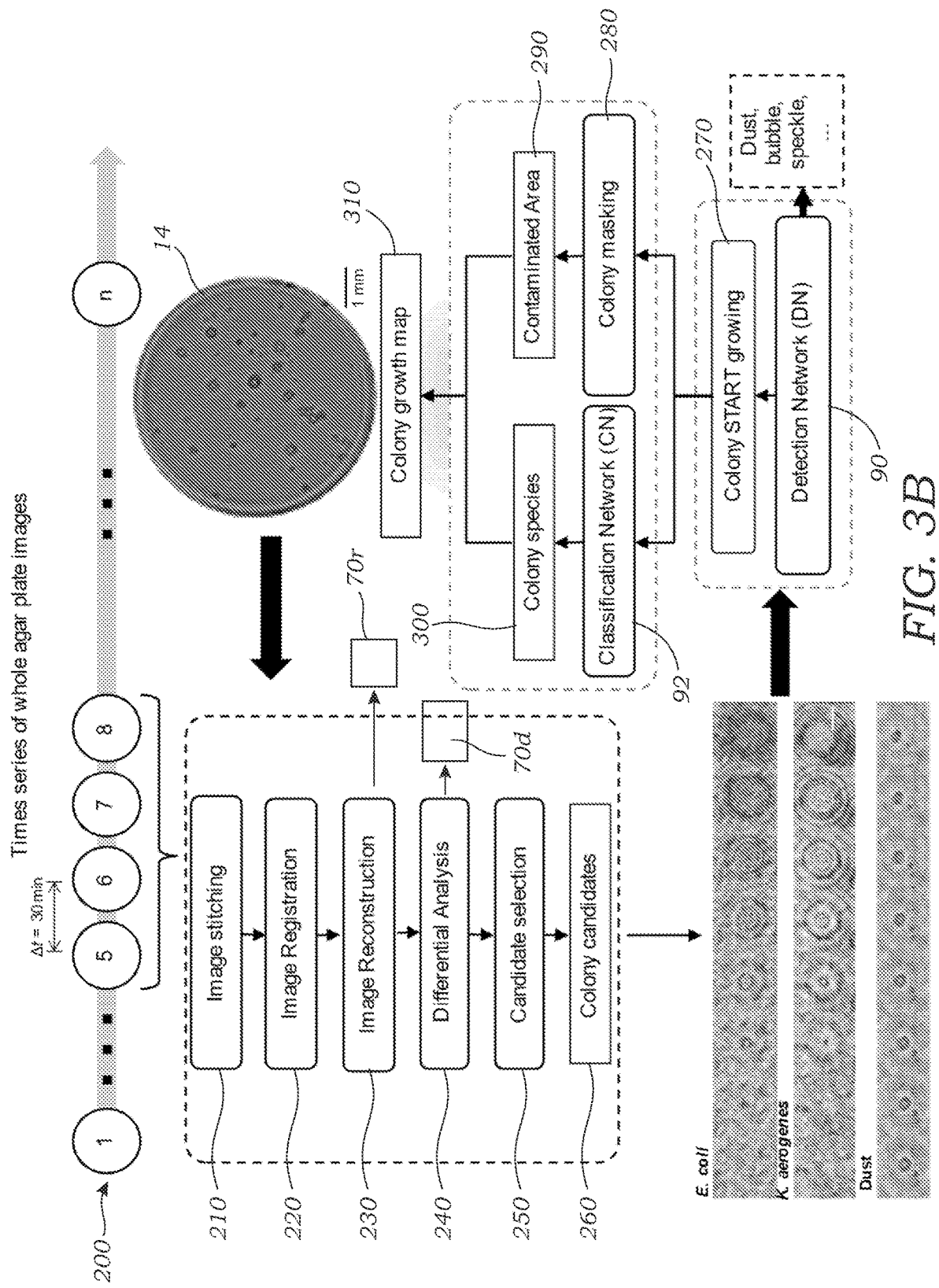
Figures 4A, 4B:
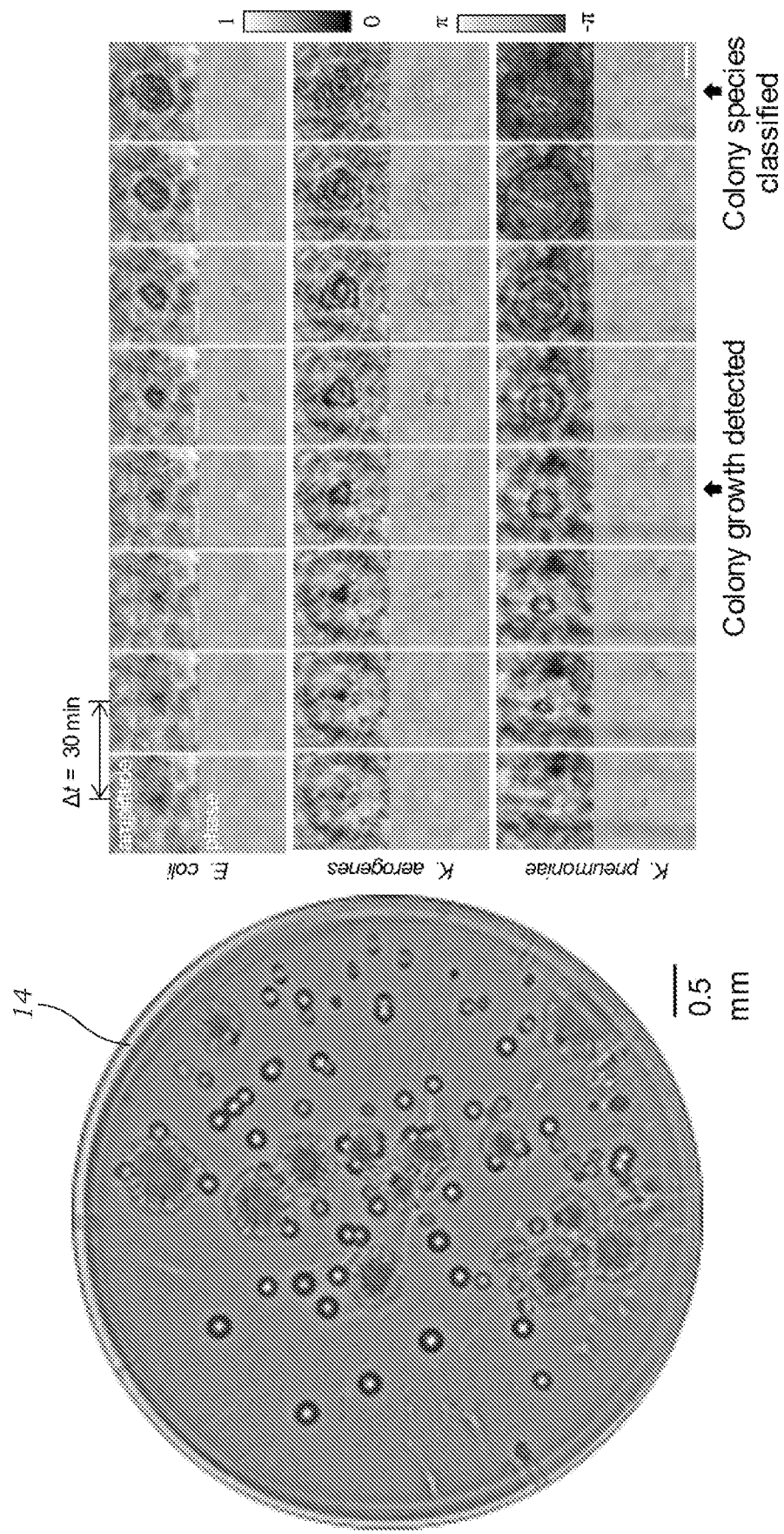
FIG. 4A illustrates an image of the whole agar-plate image of mixed *E. coli* and *K. aerogenes* colonies, after 23.5 h of incubation.
FIG. 4B illustrates example images (i.e., amplitude and phase) of the individual growing colonies detected by a trained deep neural network. The time points of detection and classification of growing colonies are annotated with arrows (above colony growth detected and colony species detected). The scale bar is 100 μm.

With reference to FIGS. 2A-2C and FIG. 3B, a periodic scanning operation is performed (e.g., each 30 minutes) wherein at least one image sensor 20 and/or the one or more growth plates 14 are moved with a moveable stage 24 in one or more dimensions to capture holographic images 70h of microorganisms 100 on the one or more growth plates 14. In one embodiment, the at least one image sensor 20 is moved while the one or more growth plates 14 are stationary (this embodiment was used for the experimental results generated herein). In another embodiment, the one or more growth plates 14 are moved. In yet another alternative, both the at least one image sensor 14 and the one or more growth plates 14 are moved. The images 70h may be obtained from a plurality of smaller image tiles of the one or more growth plates 14 with the image sensor 20 for each periodic scanning operation. FIG. 3B illustrates a time series of whole growth plate images (1 . . . 5, 6, 7, 8, n) obtained over 30-minute time intervals in operation 200. The plurality of image tiles are then digitally stitched together from the periodic scans to generate a full field-of-view (FOV) time-lapsed images of the one or more growth plates 14 with image processing software 80. This is illustrated in operation 210 in FIG. 3B. The full FOV time-lapsed images of the one or more growth plates 14 obtained over different time periods are registered with one another using the image processing software 80 as seen in operation 220 in FIG. 3B. The registered full FOV time-lapsed images are then subject to image reconstruction (e.g., using the angular spectrum back-propagation method) to generate reconstructed images 70r as seen in operation 230 in FIG. 3B. Registration may also be performed after image reconstruction in an alternative embodiment. Candidate microorganism colonies in the time-lapse reconstructed images 70r are detected with the image processing software 80 based on differential analysis in the time-lapse images 70r as seen in operation 240 in FIG. 3B. Candidates are selected (operation 250 in FIG. 3B) based on the differential image(s) with >50 connective pixels being selected that are above an intensity threshold, which is empirically set. These regions are marked as colony candidates 260 as seen in FIG. 3B, as they give a differential signal over a period of time. FIG. 3B also illustrates a time-series of reconstructed images 70r for three different objects (*E. Coli, K. aerogenes*, Dust).

With reference to FIG. 3B, in one embodiment, a first trained deep neural network 90 is also provided and executed by the image processing software 80 that is configured to detect true microorganism colonies 102 from non-microorganism objects (e.g., dust, bubbles, speckle) in the colony candidates 260. The true microorganism colonies 102 may also be counted. The true microorganism colonies 102 are then allowed to grow as seen in operation 270. As seen in FIG. 3B, the imaging and detection/classification process is performed periodically. For example, images 70h are obtained again after 30 minutes have elapsed. To prevent the double detection of true microorganism colonies 102 previously detected, these colonies 102 are subject to a masking operation 280 as they have already been detected. Likewise, known areas containing contaminants or artifacts are masked or ignored as seen in operation 290.

A second trained deep neural network 92 (e.g., classification network) is also provided and executed by the image processing software 80 that receives as an input at least one time-lapsed reconstructed image 70r and/or at least one digitally processed time-lapsed image of the true microorganism colonies 102 and outputs a species associated with each one of the detected true microorganism colonies 102 as seen in operation 300 of FIG. 3B. A colony growth map 310 may be output by the image processing software 80 which includes an image or representation of the true microorganism colonies 102 found in the one or more growth plates 14 along with indicia indicating the species of the microorganism colonies 102. This may be displayed on a display 83 or screen associate with the computing device 82. The user may view this, for example, using the GUI of the display 83 associated with the computing device 82. This is seen, for example, in the right-most image of FIG. 3A where an image of the growth plate 14 is shown along with spots or regions that have been identified containing *E. coli* and Total coliform bacteria.

EXPERIMENTAL

Results

The system 10 was demonstrated by monitoring bacterial colony growth within 60-mm-diameter agar-plates 14, and quantitatively analyzed the capabilities of the platform for early detection of bacterial growth and classification of bacterial species. The system 10 was designed to automatically detect, classify, and count *E. coli* and coliform bacteria 100 in water samples 110 using the deep learning-based platform. Throughout the training and blind testing experiments, water suspensions were used that were spiked with coliform bacteria, including *E. coli, K. aerogenes*, and *K. pneumoniae*, and chlorine stressed *E. coli*. A chromogenic agar medium designed for the specific detection and counting of *E. coli* and other coliform bacteria in food and water samples was used as a culture medium for specificity (see the Methods section for details). This chromogenic medium results in blue color for *E. coli* colonies and mauve color for the colonies of other coliform bacteria (e.g., *K. aerogenes* and *K. pneumoniae*). Additionally, it inhibits the growth of different bacteria (e.g., *Bacillus subtilis*), or yields colorless colonies in the presence of other bacteria in the sample.

Following the sample preparation method illustrated in FIG. 3A, the sample 110 is placed inside the holographic imager device 12 with the agar surface of the growth plate 14 facing the image sensor 20. After an initialization step, the system 10 automatically captures time-lapsed holographic images 70h of two separate Petri dishes 14 (covering a total sample area of 28.26×2=56.52 cm$^2$) every 30 min over a duration of 24 h starting from the incubation time; these individual hologram images 70h are digitally stitched together and rapidly reconstructed into reconstructed images 70r to reveal the bacterial growth patterns on the agar surface. The reconstructed images 70r of the sample captured at different time points are computationally processed using a differential image analysis method to automatically detect and classify bacterial growth and colonies using two different trained DNNs 90, 92 (see FIGS. 3A, 3B), which will be detailed next.

Figures 8A, 8B, 8C:
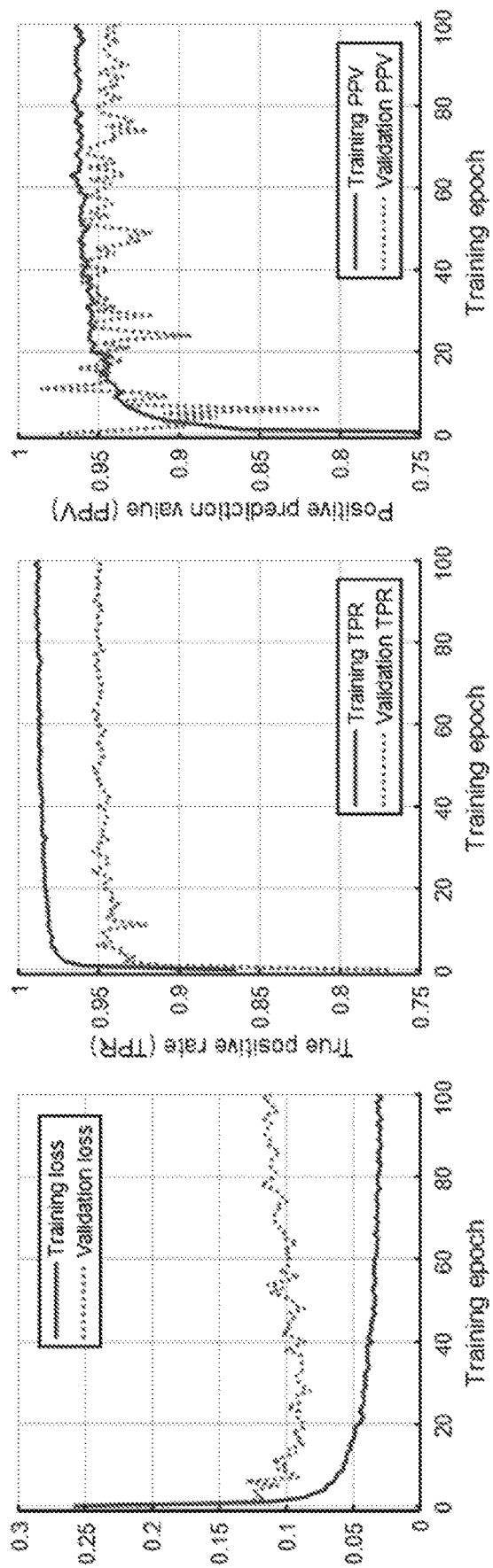
FIGS. 8A-8C illustrates training loss (FIG. 8A), true positive rate (TPR) (FIG. 8B), and positive prediction value (PPV) (FIG. 8C) curves of the neural network model for colony growth detection.
Figure 16A:
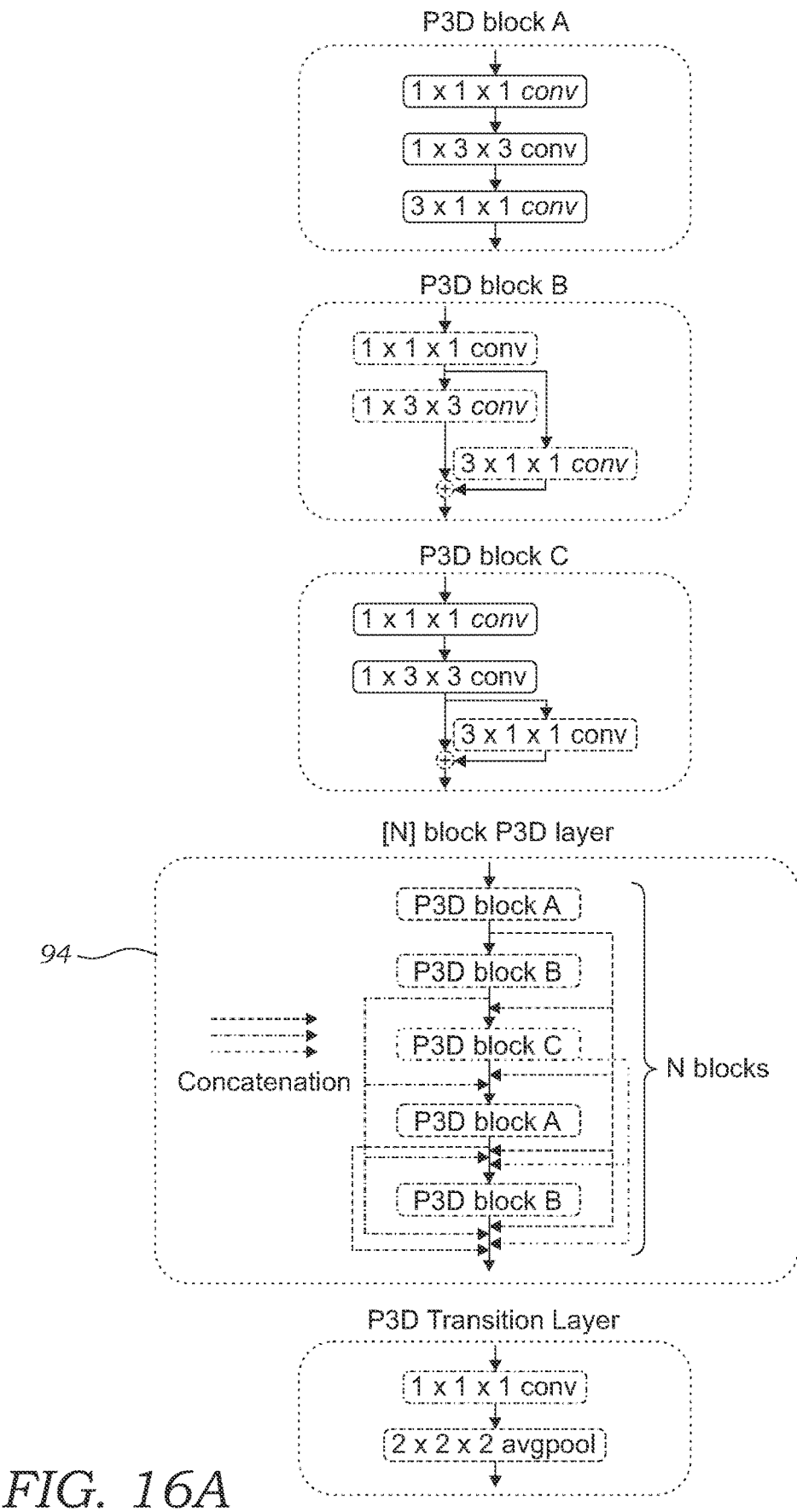
FIGS. 16A-16C schematically illustrates the pseudo-3D (P3D) DenseNet models used for the detection (Detection 93D DenseNet (FIG. 16B)) and classification (Classification 93D DenseNet (FIG. 16C)) neural networks of growing colonies using the lens-free imaging system.

Design and Training of Neural Networks for Bacterial Growth Detection and Classification A two-step framework was designed for bacterial growth detection and classification. The first step selects colony candidates with differential image analysis and refines the results with a detection DNN 90. A pseudo-3D (P3D) DenseNet architecture (FIGS. 16A and 16B) was used to process the complex-valued (i.e., phase and amplitude) time-lapse image stacks (see the Methods section). In each time-lapse imaging experiment, four (4) time-consecutive frames (4×0.5=2 h) were used as a running window for differential image analysis to extract individual regions-of-interest (ROIs) containing objects that changed their amplitude and/or phase signatures as a function of time. These initially-detected objects that were extracted by the differential analysis algorithm were either growing colonies or surface impurities, e.g., from spreading the sample on the agar surface, evaporation of air bubbles in the agar plate, or coherent light speckles. A DNN-based detection model 90 was then used to eliminate non-bacterial objects, and only kept the growing colonies 102 (i.e., the true positives), as illustrated in FIG. 3B. Sensitivity (or true positive rate, TPR) and precision (or positive predictive value, PPV) measurements were used to quantify the results. Sensitivity is defined as:

$Tpr=Tp/P$, where TP refers to the number of true positive predictions from the system, and P refers to the total number of colonies resulting from manual plate-counting after 24 h (i.e., the ground truth). Precision is defined as:

$PPV=TP/(TP+FP)$, where FP refers to the number of false positive predictions from the system. In total, 13,712 growing colonies (*E. coli*, *K. aerogenes*, and *K. pneumoniae*) and 30,000 non-colony objects captured from sixty-six (66) separate agar plates 14 were used in the training phase. Another 2,597 colonies and 13,078 non-colony objects from five (5) independent plates 14 were used as validation dataset to finalize the network models 90, and achieved a TPR of ~95% and a PPV of ~95% once the network converged, which took ~4 h of training time. Examples of the training loss and detection accuracy curves are shown in FIGS. 8A-8C.

The second step further classifies the species of the detected colonies with a classification DNN model 92 following a similar network architecture. To accommodate different growth rates of bacterial colonies 102, a longer time window was used in this classification neural network 92, containing eight (8) consecutive frames (8×0.5=4 h) for each sub-ROI. Since the bacterial growth detection network 90 uses a shorter running time window of 2 h, there is a natural 2-hour time delay between the successful detection of a growing colony and the classification of its species. The network 92 was trained with 7,919 growing colonies, which contained 3,362 *E. coli*, 1,880 *K. aerogenes*, and 2,677 *K. pneumoniae* colonies, and it was validated with 340 *E. coli*, 205 *K. aerogenes*, and 988 *K. pneumoniae* colonies from six (6) independent plates, and reached a validation classification accuracy of ~89% for *E. coli*, ~95% for *K. aerogenes*, and ~98% for *K. pneumoniae* when the network model 92 converged (FIGS. 9A-9D). After these network models 90, 92 were finalized through the training and validation data, their generalization capabilities were tested with an additional set of experiments that were never seen by the networks 90, 92 before; the results of these blind tests are detailed next.

Blind Testing Results on Early Detection of Bacterial Growth

First, the performance of the system 10 was blindly tested in early detection of bacterial colonies 102 with nine-hundred sixty-five (965) colonies from fifteen (15) plates that were not presented during the network training or validation stages. The predicted number of growing colonies 102 on the sample within the first 14 h of incubation were compared against a ground truth colony count obtained from plate counting after 24 h of incubation time. Each of the three (3) sensitivity curves (FIGS. 5A-5C) were averaged across repeated experiments for the same species, e.g., four (4) experiments for *K. pneumoniae*, seven (7) experiments for *E. coli*, and four (4) experiments for *K. aerogenes*, so that each data point was calculated from ~300 colonies 102. The results demonstrated that the system 10 was able to detect 80% of true positive colonies 102 within ~6.0 h of incubation for *K. pneumoniae*, ~6.8 h of incubation for *E. coli*, and ~8.8 h of incubation for *K. aerogenes*, respectively. It further detected 90% of true positives after ~1 additional hour of incubation, and >95% of the true positive colonies 102 of all of the three (3) species within 12 h. The results also reveal that the early detection sensitivities in FIGS. 5A-5C are dependent on the length of the lag phase of each tested bacteria species, which demonstrates inter-species variations. For example, *K. pneumoniae* started to grow earlier and faster than *E. coli* and *K. aerogenes*, whereas *K. aerogenes* did not reach to a detectable growth size until 5 h of incubation. Furthermore, when the tails of the sensitivity curves are examined, one can find out that some of the *E. coli* colonies 102 showed late "wake-up" behavior, as highlighted by the arrow in FIG. 5B. Although most of the *E. coli* colonies 102 were detected within ~10 h of incubation time, some of them did not emerge until ~11 h after the start of the incubation phase.

The false positive rate of the system 10 was also quantified with the PPV curve as shown in FIG. 5D, which was averaged across all the experiments covering all the species, i.e., nine-hundred sixty-five (965) colonies 102 from fifteen (15) agar-plates 14. The precision can be low at the beginning of the experiments (the first 4 h of incubation), because the number of detected true positive colonies 102 is very small, especially for *K. aerogenes*. This means even a single false positive-detected colony can dramatically affect the precision calculation. Nevertheless, the precision quickly rises up to ~100% within 6 h of incubation and is maintained at 99.2-100% for all the tested species after 7 h of incubation.

It should be emphasized here that the results presented in FIGS. 5A-5E represent the lower limits of the detection capabilities of the system 10 since these sensitivities were calculated with regard to the number of true positive colonies 102 after 24 h of incubation, whereas some of these colonies 102 actually did not exist at the early stages due to delayed growth; stated differently in some cases, there were no colonies 102 present at the early stages of the incubation period. It should also be noted that the rising sensitivity curves in the results stand for the emergence of new bacterial colonies 102, in addition to the growth of colonies 102. Even though the sensitivity curves converge to flat lines after 12 h, the colonies 102 keep growing exponentially until much later. Therefore, the system 10 detects emerging colonies 102 at an early stage, when they first appear, forming micro-scale features invisible to the naked eye.

These observations also indicate that the system 10 can be very effective and used for high-throughput quantitative studies to better understand microorganism behavior under different conditions, such as the evaluation of the differences in growth rates between stressed bacteria (e.g., under nutrient deprivation or chlorine treatment) and normal bacteria. There are several reasons to detect and enumerate chlorine stressed or injured coliform bacteria. First, the detection of injured *E. coli* or total coliform bacteria is directly related to the sensitivity of the detection platform. For an effective and sensitive detection system 10, the false negative results should be avoided for public health safety. Another important reason is that the detection of injured *E. coli* or low numbers of *E. coli* in water samples is correlated to *Salmonella* outbreaks, a foodborne pathogen causing 1.2 million illnesses and ~500 deaths per year in the United States, which forms an indirect indicator of contamination in irrigation water. To evaluate the capabilities of the system 10 to detect injured bacteria, three (3) agar plates 14 were prepared and imaged containing chlorine-stressed *E. coli* (see the Methods section), and characterized their growth using the detection workflow as summarized in FIG. 5E. The results indicate that the system 10 can detect colony formation for chlorine-stressed *E. coli* on average with a ~2 h delay compared to the regular *E. coli* strain.

Blind Testing Results on Classification of Growing Bacteria

In addition to providing significant detection time savings while also achieving a very good sensitivity and precision for early detection of bacterial growth, the system 10 and method also provides automated classification of the corresponding species of the detected bacteria using a trained neural network 92. Therefore, an additional advantage of the system 10 is its capability to further classify total coliform sub-species, which is not possible with traditional agar-plate counting methods. For example, both *K. pneumoniae* and *K. aerogenes* colonies appear mauve in the agar-plates. However, since the classification neural network 92 does not only rely on the byproducts of the colorimetric reactions, it can successfully distinguish between different species based on their unique spatiotemporal growth signatures acquired by the system 10 at the micro-scale.

FIGS. 6A-6C shows the blind testing results on species classification using the same experiments reported in the blinded early-detection tests, containing nine-hundred sixty-five (965) colonies 102 of three (3) different species from fifteen (15) agar-plates 14. In these results, if a colony 102 had not been detected in the previous step (i.e., a false negative event compared to the 24 h reading), it was naturally not sent to the classification neural network 92. The recovery rate was defined as the number of colonies 102 correctly classified into their corresponding species using the system, divided by the total number of colonies 102 counted after 24 h. As the classification of each individual colony 102 is an independent event, the recovery rate was calculated for each bacteria species (reported in FIGS. 6A-6C) using all of the colonies 102 detected in the previous step, i.e., 336, 280, and 339 colonies of *E. coli, K. aerogenes*, and *K. pneumoniae*, respectively. The shaded area in each curve represents the highest and lowest recovery rates found in all the corresponding experiments at each time point. The classification neural network 92 correctly classified ~80% of all of the colonies within ~7.6 h, ~8 h, and ~12 h for *K. pneumoniae, E. coli,* and *K. aerogenes,* respectively. Once again it should be emphasized that the results presented in FIGS. 6A-6C represent the lower limits of the classification capabilities of the system 10 since the ground truth is acquired after 24 h of incubation. In reality, at various earlier time points within the incubation period, there was no growth for certain regions of the plates 14, which exhibited significantly delayed growth. To further demonstrate the classification performance of the trained neural network 92 in a manner that is decoupled from the sensitivity of the previous detection network 90, the classification confusion matrix is reported in FIG. 6D for all the colonies 102 that were sent to the classification network 92 for blind testing at 12 h after the start of the incubation. The trained network 92 achieved classification accuracies of ~97.2%, ~84.0%, and ~98.5% for *E. coli, K. aerogenes,* and *K. pneumoniae*, respectively.

Limit of Detection as a Function of the Total Test Time

Figure 7A:
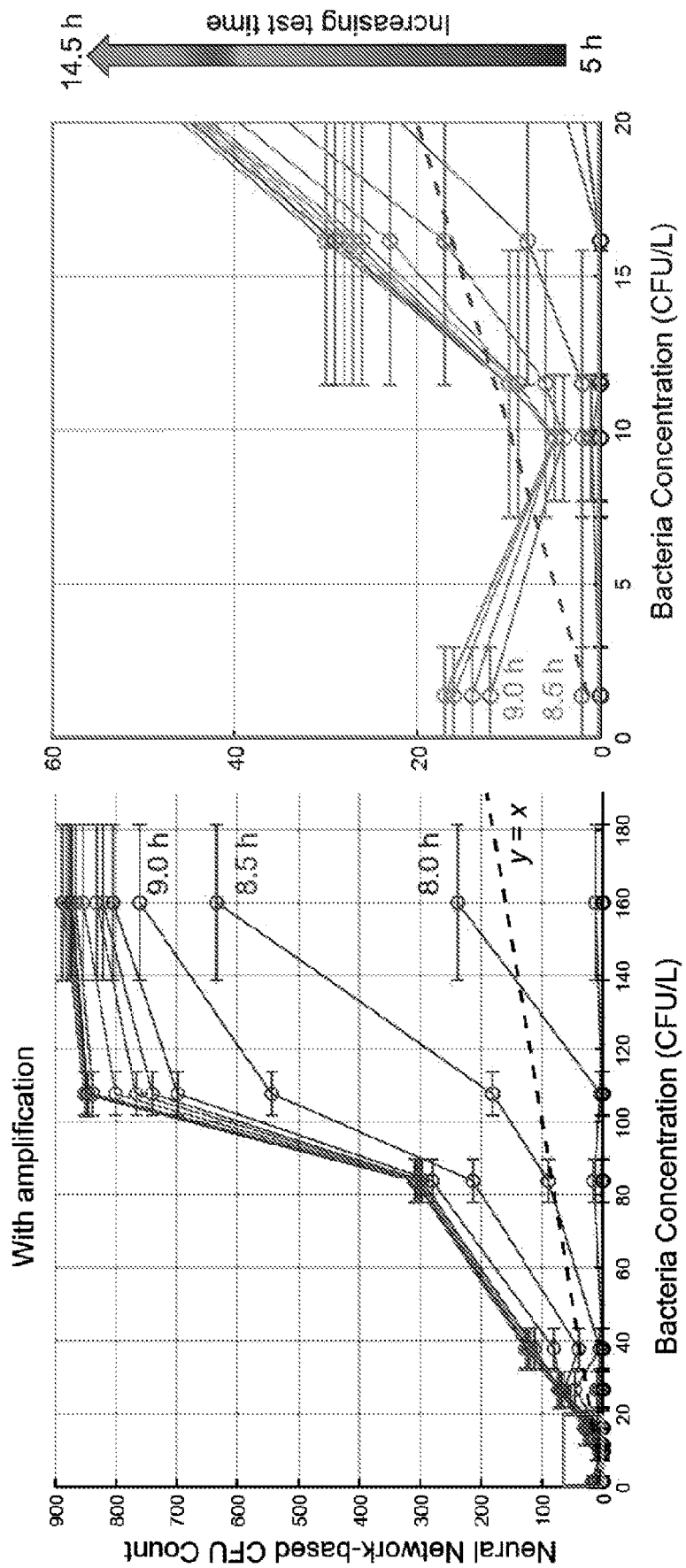
FIGS. 7A-7D illustrates the quantification of the limit of detection (LOD) of the system.
Figure 10:
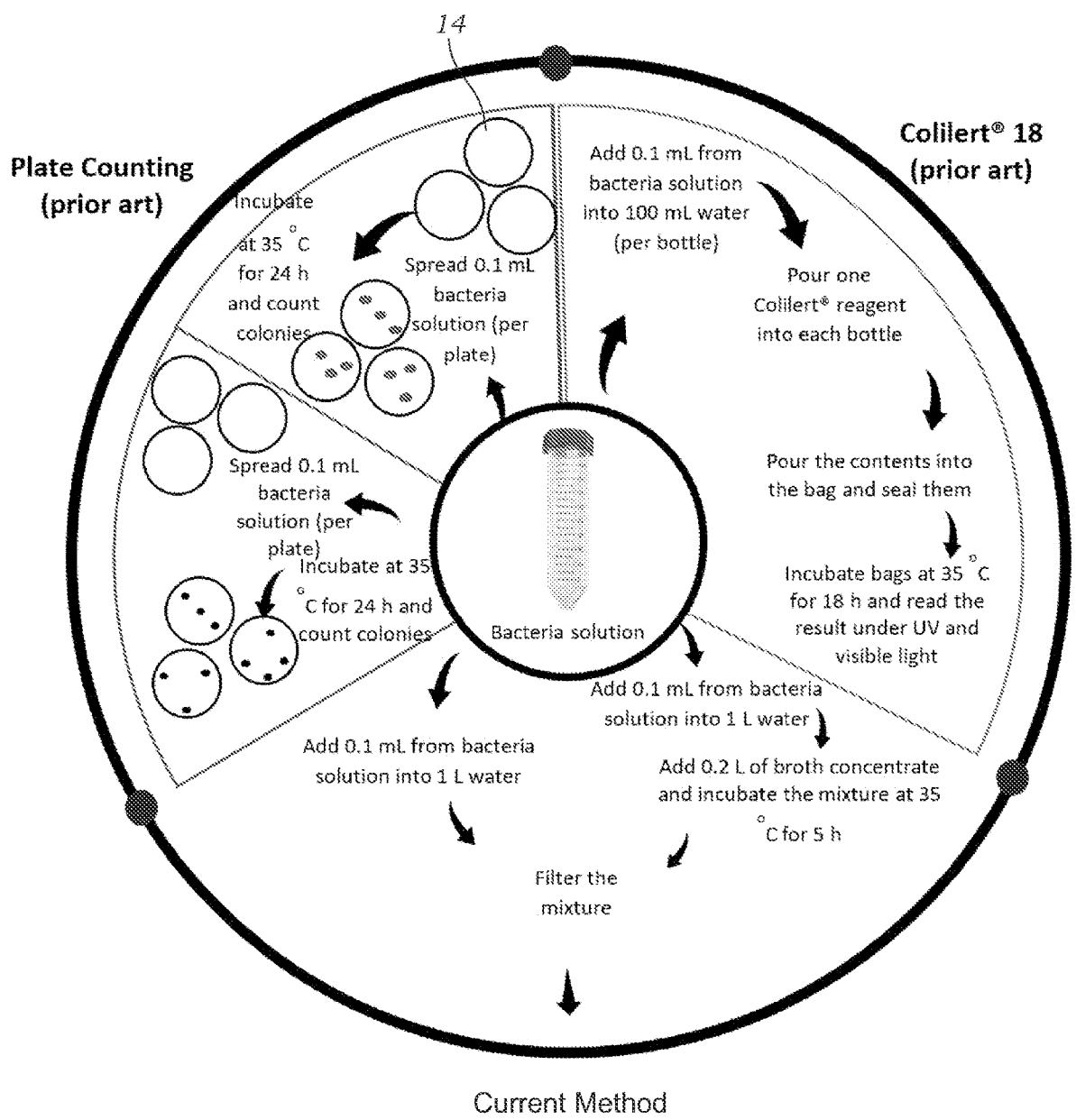
FIG. 10 illustrates a comparison of the major steps/operations involved in each one of the three different methods analyzed herein. This includes plate counting (prior art), Colilert® 18 (prior art), and the current method/system (current method).

The detection limit of the system 10 was further quantified and compared its performance against both Colilert® 18, which is an EPA approved method, and traditional plate counting (Table 1 and FIG. 10). To make up for the CFU loss during the sample transfer from the water suspension to the filter membrane, a signal amplification step was introduced by pre-incubating the water sample under test, mixing it with a growth medium for 5 h at 35° C. before the filtration step (see the Methods section for details). For each measurement, two (2) agar plates 14 were prepared and monitored at the same time for comparison, one of which was for the sample amplified with 5-h pre-incubation step before the filtering, while the other one was for the sample directly filtered and transferred to the agar plate 14 (see FIG. 10). Both plates 14 were incubated for the same amount of time at each imaging time point to provide a fair comparison between the two. The measurements were repeated using different concentrations of *E. coli* suspensions; these concentrations were compared to the average of three replicates of the same samples prepared using the Colilert®-18 method (FIG. 10). As shown in FIGS. 7A and 7D, the system 10 is able to surpass the sensitivity of Colilert®-18 within ~8 h in total (including the time for signal amplification, sample concentration, and time-lapse imaging, altogether) and reach >2 times the sensitivity of Colilert®-18 in ~9 h. The LOD of the system 10 was also quantified by preparing and imaging three (3) agar plates 14 without bacteria, which show on average <1 CFU count from the setup throughout the test period from 5 h to 14.5 h (FIG. 7C), revealing a detection limit of μ+3 σ=~2 CFU per test, where μ and σ refer to the mean and standard deviation of the detected CFU count, respectively. Due to the effective signal amplification enabled by the pre-incubation step, even with the lowest bacterial concentration of ~1 CFU/L, the system 10 was able to detect 2 CFU at 8.5 h, and 12 CFU at 9 h; in comparison, for the same contaminated water sample Colilert® 18 achieved 1.4±1.6 CFU/L after 18 hours of incubation. Furthermore, for all the concentrations experimented with (~1-160 CFU/L), the system 10 successfully detected more than 2 CFU per test in ≤9 h of test time, including all the necessary steps i.e., the time for signal amplification, sample concentration, and time-lapse imaging; these results reveal that the system 10 with a pre-incubation step achieves a detection limit of ~1 CFU/L within <9 h of total test time.

performance a 4× objective lens with a numerical aperture (NA) of ~0.1. Compared to the system, which takes 87 s to scan an agar plate, a traditional lens-based bright-field microscope using a 4× objective lens would approximately take ~128 min to scan a plate with the same diameter (60 mm), owing to the requirement for mechanical axial focusing (see Table 2).

TABLE 1

| Colilert ®-18 | | | | | Plate counting (TSA plates) | | | | | Plate counting (ECC ChromoSelect Selective Agar plates) | | | | |
|---|---|---|---|---|---|---|---|---|---|---|---|---|---|---|
| R1* | R2* | R3* | Ave. | Std. dev. | R1† | R2† | R3† | Ave. | Std. dev. | R1† | R2† | R3† | Average | Std. deviation |
| 172.3 | 172.3 | 135.4 | 160.00 | 21.30 | 169 | 162 | 198 | 176.33 | 19.09 | 164 | 137 | 140 | 147.00 | 14.80 |
| 11 | 17.3 | 20.1 | 16.13 | 4.66 | 15 | 18 | 14 | 15.67 | 2.08 | 17 | 13 | 17 | 15.67 | 2.31 |
| 225.4 | 166.4 | 228.2 | 206.67 | 34.90 | 228 | 260 | 246 | 244.67 | 16.04 | 245 | 241 | 221 | 235.67 | 12.86 |
| 8.6 | 8.5 | 12.1 | 9.73 | 2.05 | 4 | 4 | 5 | 4.33 | 0.58 | 2 | 5 | 11 | 6.00 | 4.58 |
| 37.9 | 43.5 | 32.3 | 37.9 | 5.6 | 52 | 37 | 30 | 39.67 | 11.24 | 35 | 28 | 36 | 33.00 | 4.36 |
| 3.1 | 1 | <1 | 2.05 | 1.48 | 3 | 1 | 0 | 1.33 | 1.53 | 3 | 3 | 2 | 2.67 | 0.58 |
| 107.6 | 113.7 | 101.7 | 107.67 | 6.00 | 76 | 116 | 99 | 97.00 | 20.07 | 150 | 134 | 123 | 135.67 | 13.58 |
| 172.3 | 210.5 | 121.1 | 167.97 | 44.86 | 165 | 165 | 141 | 157.00 | 13.86 | 169 | 171 | 164 | 168.00 | 3.61 |

R is for replicate sample
*CFU/100 mL
†CFU/0.1 mL

Figures 7B, 7C:
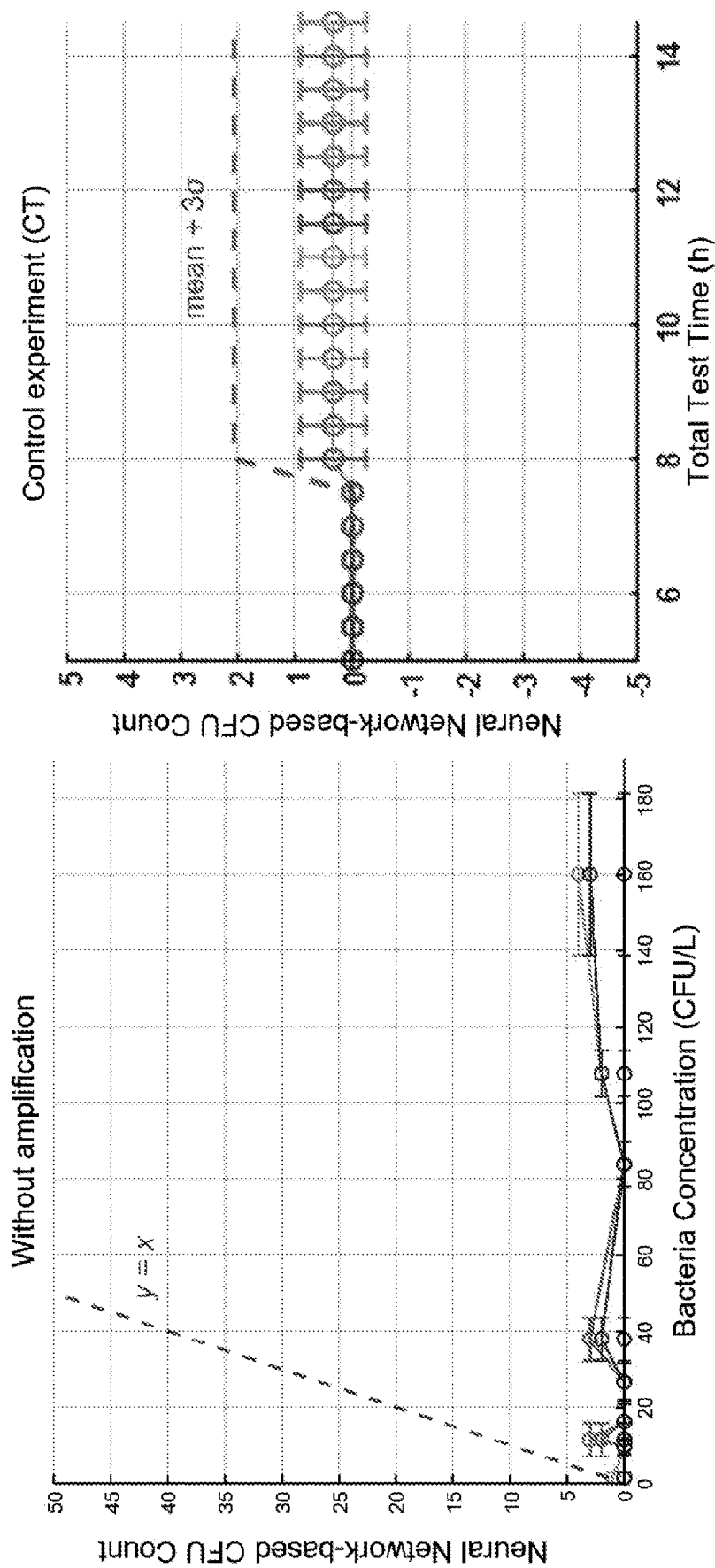
Figure 7D:
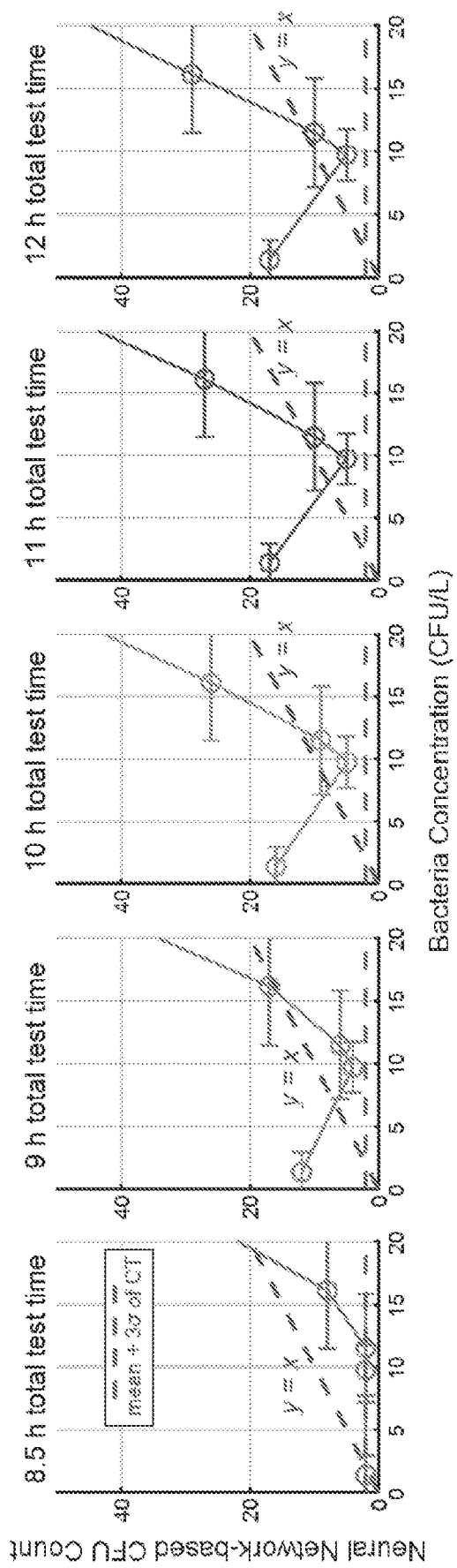
Figure 11A:
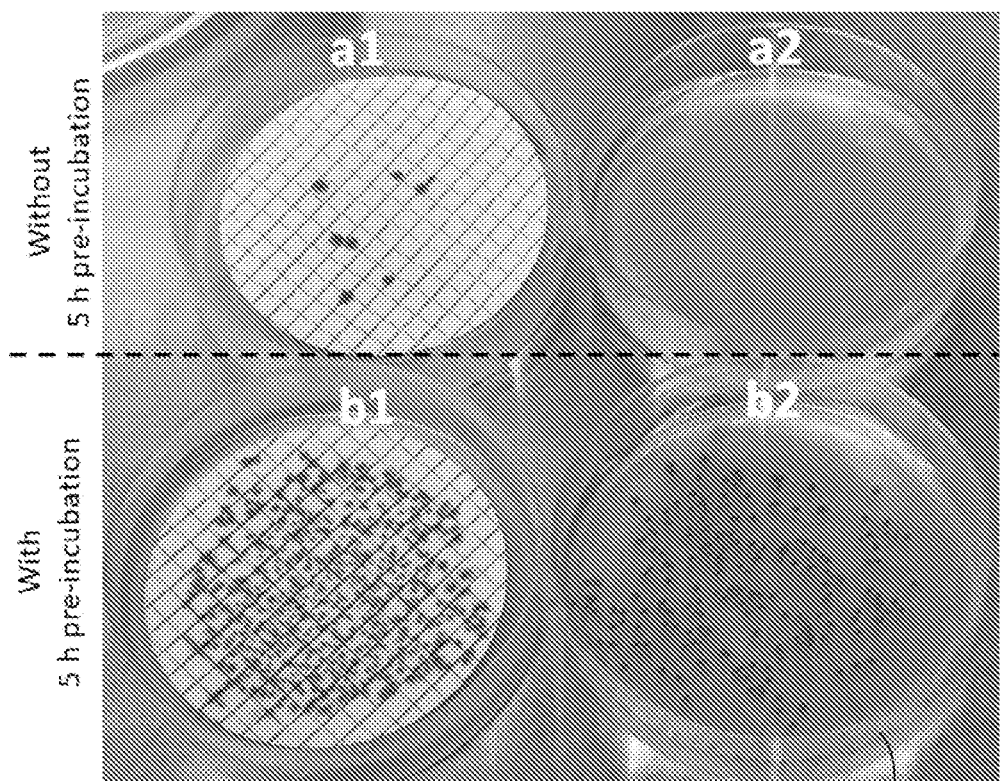
FIGS. 11A and 11B illustrate example photos of CHROMagar™ ECC plates for two different bacterial concentrations of (FIG. 11A) 37.9±5.6 CFU/L, (FIG. 11B) 160±21.3 CFU/L. a1) No pre-incubation, after transferring bacteria from filter membrane to the agar plate and incubation at a benchtop incubator for 24 h. a2) No pre-incubation, transferred bacteria from the filter membrane in the photo of a1, incubated at the lens-free imaging setup for 24 h. b1) 5 h pre-incubation, after transferring bacteria from filter membrane to the agar plate and incubation at a benchtop incubator for 19 h (total incubation time: 5+19=24 h). b2) 5 h pre-incubation, transferred bacteria from the filter membrane in the photo of a1, incubated at the lens-free imaging setup for 19 h (total incubation time: 5+19=24 h).
Figure 11B:
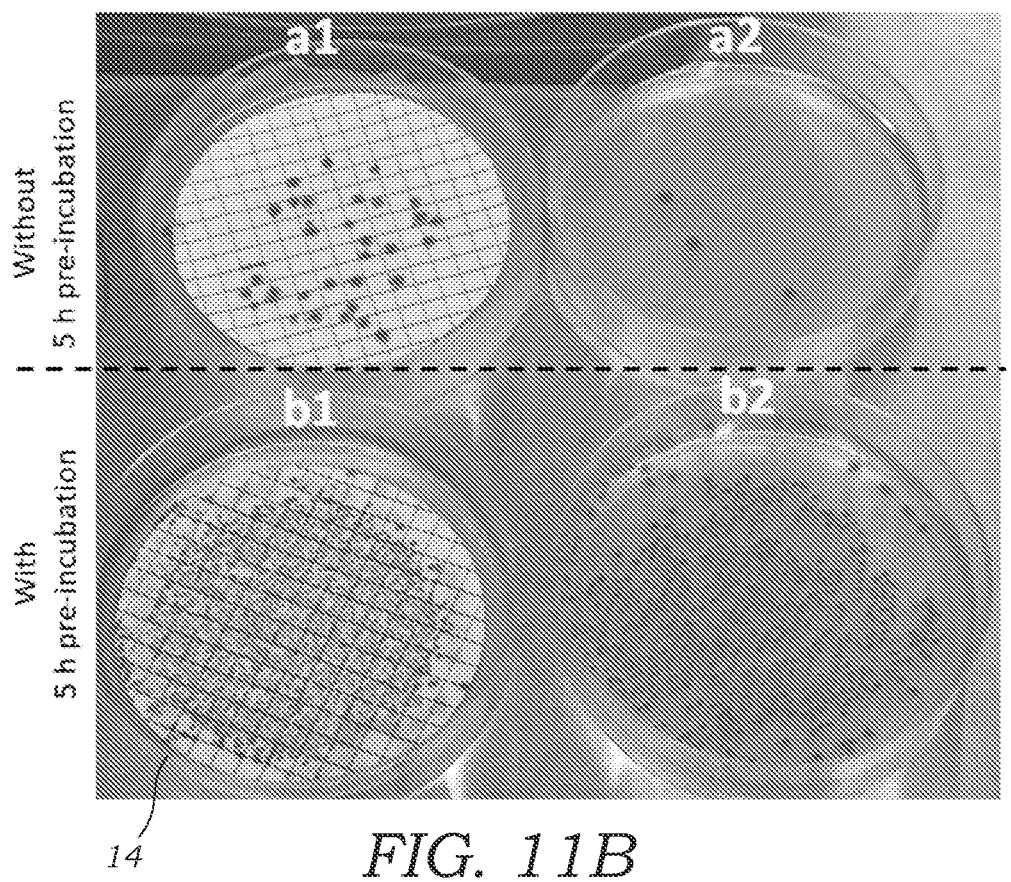

It can be observed in FIG. 7B that without the signal amplification enabled by pre-incubation, the detection performance is negatively affected due to the low transfer rate of bacteria from the container to the agar plate 14 (also see FIGS. 11A, 11B). FIG. 7C shows the control experiment (CT). In general, the sensitivity and LOD of the method might be further improved by increasing the pre-incubation time of the water-broth mixture, at the cost of an increase in the total time to achieve automated detection and classification.

A system 10 for the early detection and classification of microorganisms 100 (e.g., bacterial colonies 102) is disclosed, which is fully compatible with the existing EPA-approved methods and can be integrated with them to considerably improve the analysis of agar plates 14. The system 10 can automatically detect bacterial growth as early as in 3 h and can detect 90% of bacterial colonies 102 within 7-10 h (and >95% within 12 h), with a precision of 99.2-100%. The system 10 also correctly classifies ~80% of all of the tested bacterial colonies 102 within 7.6, 8.8, and 12 h, for *K. pneumoniae*, *E. coli*, and *K. aerogenes*, respectively. These results present a total time saving of more than 12 h as compared to the gold-standard methods (e.g., Colilert test and Standard Method 9222 B), which require 18-24 h. In addition to automated detection of live bacteria and species classification, the rich spatio-temporal information embedded in the holographic images 70h can be used for more advanced analysis of water samples and microbiology research in general.

Figures 12A, 12B, 12C:
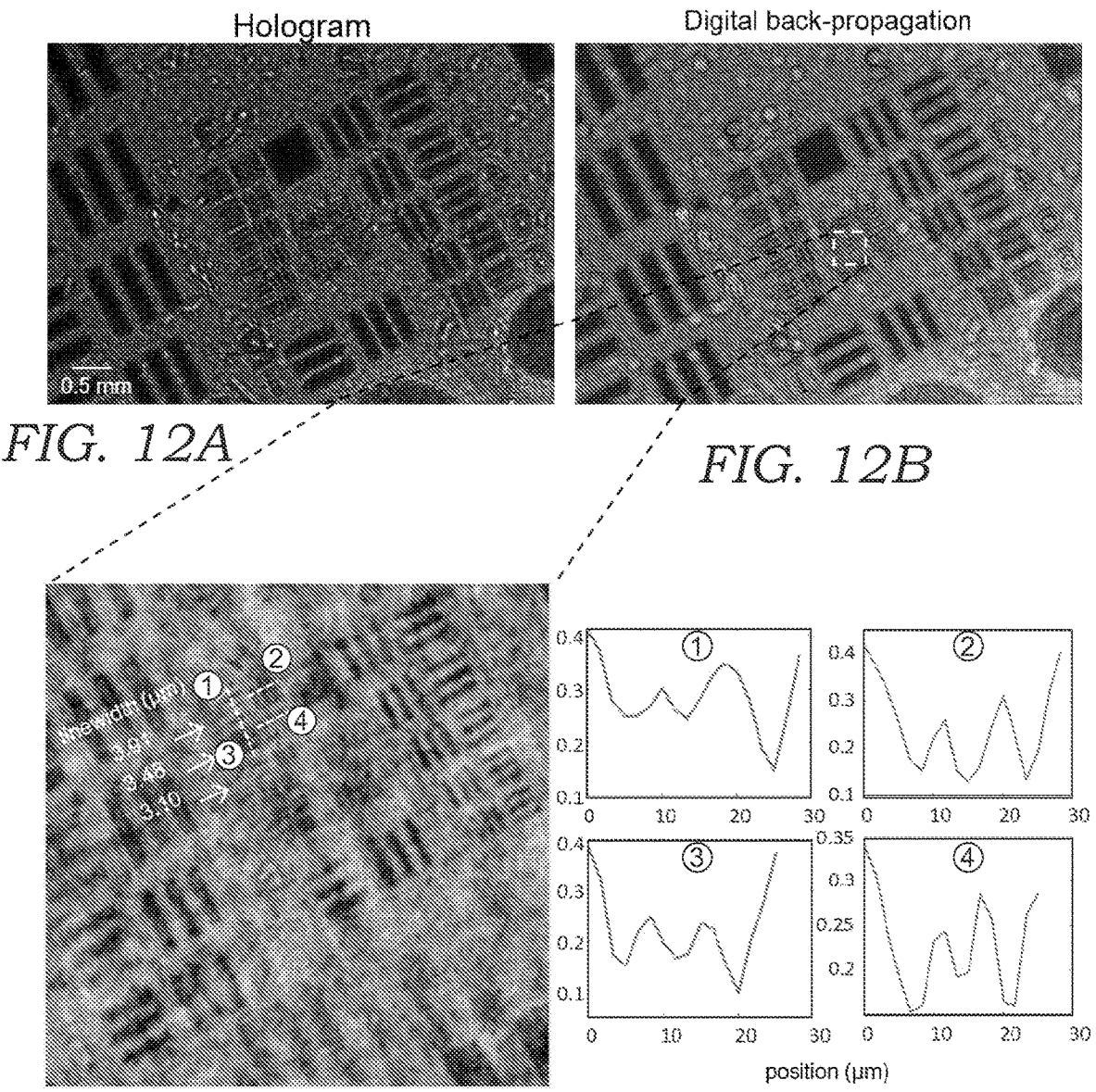
FIGS. 12A-12C illustrates the resolution characterization of the lens-free bacterial colony detection system.

Another advantage of this system 10 is its high-throughput imaging capability of agar plates 14. The system 10 performs a 242-tile-scan within 87 s per agar plate 14, corresponding to a raw image scanning throughput of ~49 $cm^2$/min. To leave sufficient data redundancy for image post-processing, a relatively large overlap of 30% on each side of the acquired holographic image 70h was set, which reduces the effective imaging throughput of the platform to ~24 $cm^2$/min. As the system 10 is based on lens-free holographic microscopy, it does not require mechanical axial focusing at each position, and instead auto-focuses onto the object plane computationally. The spatial resolution of the system 10 was characterized by imaging a resolution test target, as shown in FIGS. 12A-12C, achieving a linewidth resolution of ~3.5 μm, roughly equivalent to the

TABLE 2

| Configuration | Current System 10 | Bright-field microscope (4×/0.1 NA objective lens) |
|---|---|---|
| Field of view (FOV) per image ($mm^2$) | 29.4 | 14.4 |
| Total FOV scanned ($mm^2$) | ~3491 | ~2977 |
| Total imaging time per agar plate (min) | ~1.5 | 128 |
| Effective pixel count (million) | 570 | 435 |
| Observation depth (μm) | >20,000 | 3,000 (with 20 μm accuracy) * |

Another important advantage of the system 10 is the minimum requirement for optical alignment; the presented system 10 is tolerant towards structural changes, such as variations in the sample-to-sensor distance or the illumination angle. The computational refocusing capability also enables screening of thick samples, e.g., melted agar-plates 14. An example of a 3D sample is illustrated in FIGS. 13A-13C, where *E. coli* colonies 102 are formed at different depths inside the solid culture medium having a thickness of ~5 mm. For example, the colony 102 marked with "A" grew at ~2170 μm measured from the surface of the agar, whereas the colony 102 marked with "B" was on the agar surface. The system 10 localizes colonies 102 growing at different depths within a 3D culture medium using a single hologram measurement at each scanning position. However, it is a non-trivial task to image a 3D sample using a conventional lens-based microscope, because of the time required for mechanical focusing, and the refractive index mismatch between the culture medium and the air, which degrades the image resolution as a result of aberrations. Therefore, the corresponding brightfield microscopy images of the whole plates could only be acquired after 24 h of incubation.

The system 10 also employs a modular design which is scalable to a larger sample size and a smaller tile-scan time interval. The monitoring field of view (FOV) of this platform is fundamentally limited by the image acquisition time and the stage moving speed. With further optimization of the hardware and control algorithms, an imaging throughput of >50 cm$^2$/min can be reached. Alternatively, multiple image sensors 20 can be installed and connected to a single computing device 82 for high-throughput parallel imaging. In the current implementation, the image processing for each time interval takes ~20 min, and fits well into the 30 min measurement period between each scan. In case a shorter time interval is desired, an image processing procedure implemented using MATLAB and Python/PyTorch programming environments can be further sped up by programming in C/C++. With the help of graphic processing units (GPUs) 84, one can expect >10-fold time savings in computation.

This unique system 10 is integrated with an incubator 16 to keep the agar plates at a desired temperature. The incubator 16 is a thermal glass plate which contains uniform lines of optically clear indium tin oxide (ITO) electrode for heating the sample placed on top. It is controlled with control circuitry 26 (e.g., a controller), which is lightweight. Throughout the experiments, the temperature at the agar surface where bacteria grew was set at ~38° C., so that all of the tested bacteria species could grow and develop colonies 102. This temperature was not optimized to promote the growth of a specific species. Therefore, adjustment of the incubation environment, its temperature and humidity can be used to further accelerate colony growth and help us achieve earlier detection and identification of specific bacterial colonies 102. Another important parameter for growth of microorganisms is humidity. The system 102 can also be integrated with a controlled humidity chamber (now shown) for better control and analysis of growth dynamics of various microorganisms.

In summary, a deep learning-based live microorganism monitoring system 10 is disclosed for early detection of growing colonies and classification of colony species using deep learning. The system 10 was evaluated using three (3) types of bacteria, i.e., *E. coli, K. aerogenes*, and *K. pneumoniae*, and achieved >12 h time savings for both the early detection and the classification of growing species as compared to the gold standard EPA-approved methods. Of course, the system 10 may be used with other strains of bacteria (or other microorganisms 100) and is not limited to those specifically disclosed herein. Achieving an LOD of ~1 CFU/L in <9 hours, this versatile system will not only benefit water and food quality monitoring, but also provide a powerful tool for microbiology research.

Methods

Sample Preparation

Safety practices: All the bacterial cultures and the experiments performed were done at the UCLA Biosafety Level 2 laboratory, in accordance with the environmental, health, and safety rules of the University of California, Los Angeles.

Studied organisms: *E. coli* (Migula) Castellani and Chalmers (ATCC® 25922™) (risk level 1), *K. aerogenes* Tindall et al. (ATCC® 49701™) (risk level 1), and *K. pneumoniae* subsp. *pneumoniae* (Schroeter) Trevisan (ATCC®13883™) (risk level 2) were used as the culture organisms.

Preparation of poured agar plates: CHROMagar™ ECC (product no. EF322, DRG International, Inc., Springfield, NJ, USA) chromogenic substrate mixture was used as the solid growth medium for the detection of *E. coli* and total coliform colonies. 8.2 g of CHROMagar™ ECC was mixed with 250 mL of reagent grade water (product no. 23-249-581, Fisher Scientific, Hampton, NH, USA), using a magnetic stirrer bar. The mixture was then heated to 100° C. on a hot plate while being stirred regularly. After cooling the mixture to ~50° C., 10 mL of the mixture was dispensed into Petri dishes (60 mm×15 mm) (product no. FB0875713A, Fisher Scientific, Hampton, NH, USA). The agar plates 14 were allowed to solidify, sealed using a parafilm (product no. 13-374-16, Fisher Scientific, Hampton, NH, USA), and covered with aluminum foil to keep them in dark before use. They were stored at 4° C. and were used within two weeks of preparation.

Preparation of melted agar plates: 3.28 g of CHROMagar™ ECC was mixed with 100 mL of reagent grade water using a magnetic stirrer bar, and the mixture was heated to 100° C. After the mixture cooled to ~40° C., 1 mL of bacterial suspension was mixed with the agar and dispensed into the Petri dishes. The plates were either incubated in a benchtop incubator (product no. 51030400, ThermoFisher Scientific, Waltham, Mass., USA) or in the imaging platform (for monitoring the bacterial growth digitally).

Tryptic soy agar was used to culture *E. coli* at 37° C. and *K. aerogenes* at 35° C., and nutrient agar to culture *K. pneumoniae* at 37° C. 20 g of tryptic soy agar (product no. DF0369-17-6, Fisher Scientific, Hampton, NH, USA) or 11.5 g of nutrient agar (product no. DF0001-17-0, Fisher Scientific, Hampton, NH, USA) were suspended in 500 mL of reagent grade water using a magnetic stirrer bar. The mixture was boiled on a hot plate, and then autoclaved at 121° C. for 15 min. After the mixture cooled to ~50° C., 15 mL of the mixture was dispensed into the Petri dishes (100 mm×15 mm) (product no. FB0875713, Fisher Scientific, Hampton, NH, USA), which were then sealed with parafilm and covered with aluminum foil to keep them in dark before use. They were stored at 4° C. until use.

Preparation of chlorine stressed *E. coli* samples: *E. coli* was grown on tryptic soy agar plates and incubated for 48 h at 37° C. 50 mL disposable centrifuge tubes were used as a sample container and the sample size was 50 mL. 500 mL reagent grade water was filtered for sterilization using a disposable vacuum filtration unit (product no. FB12566504, Fisher Scientific, Hampton, NH, USA). A fresh chlorine suspension was prepared in a 50 mL disposable centrifuge tube to have a final concentration of 0.2 mg/mL using sodium hypochlorite (product no. 425044, Sigma Aldrich, St. Louis, Mo., USA), mixed vigorously, and covered with aluminum foil. 10% [w/v] sodium thiosulfate (product no. 217263, Sigma Aldrich, St. Louis, Mo., USA) in reagent grade water was prepared and 1 mL of the solution was filtered using a sterile disposable syringe and a syringe filter membrane (product no. SLGV004SL, Fisher Scientific, Hampton, NH, USA) for sterilization. Water suspensions were prepared by spiking *E. coli* into filtered water samples. 50 µL of chlorine suspension (i.e., 0.2 ppm) was added to the test water sample and a timer counted the chlorine exposure time. The reaction was stopped at 10 minutes of chlorine exposure by adding 50 µL sodium thiosulfate into the test water sample and mixed vigorously immediately to stop the chlorination reaction. CHROMagar™ ECC plates were inoculated with 200 p.L of chlorine stressed suspension, dried in the biosafety cabinet for at most 30 min and then placed on the setup for lens-free imaging. In addition, three TSA plates and one ECC ChromoSelect Selective Agar plate (product no. 85927, Sigma Aldrich, St. Louis, MO, USA) were inoculated with 1 mL of the control sample (not exposed to chlorine) and 0.2 ppm chlorine stressed *E. coli* water sample and dried under biosafety cabinet for about 1-2 h with gentle mixing of Petri dishes with some time intervals. After drying, the plates were sealed with parafilm and incubated at 37° C. for 24 h. After the incubation, the bacterial colonies grown on the agar plates were counted and

*E. coli* concentrations of control samples and the chlorine stressed *E. coli* samples were compared. If the achieved reduction in colony count was between 2.0-4.0 log, then the images of CHROMagar™ ECC plates captured using the lens-free imaging platform were used for further analysis.

Preparation of culture plates for lens free imaging: A bacterial suspension in a phosphate buffer solution (PBS) (product no. 20-012-027, Fisher Scientific, Hampton, NH, USA) was prepared every day from a solid agar plate incubated for 24 h. The concentration of the suspension was measured using a spectrophotometer (model no. ND-ONE-W, Thermo Fisher), and the suspension was then diluted in the PBS to have a final concentration of 1-200 CFU per 0.1 mL. 100 µL of the diluted suspension was spread on an CHROMagar™ ECC plate using an L-shaped spreader (product no. 14-665-230, Fisher Scientific, Hampton, NH, USA). The plate was covered with its lid, inverted, and incubated at 37° C. in the optical platform (FIGS. 2A-2C and 3A, 3B).

Preparation of concentrated broth: 180 g of tryptic soy broth (product no. R455054, Fisher Scientific, Hampton, NH, USA) was added into 1 L reagent grade water and heated to 100° C. by continuously mixing using a stirrer bar. The suspension was then cooled to 50° C. and filter sterilized using a disposable filtration unit. The broth concentrate was stored at 4° C. and used in one week after preparation.

Preparation of samples for comparison measurements: The performance of the method was evaluated in comparison to Colilert® 18, which is an EPA-approved enzyme based analytical method for several types of regulated water samples (e.g., drinking water, surface water, ground water) to detect *E. coli* and plate counting using TSA plates and ECC ChromoSelect Selective Agar plates (FIG. 10). Two bottles of 1 L of reagent grade water were filtered using the disposable vacuum filtration units and 0.2 L of the concentrated broth was added into one of the 1 L sample bottles. The bottles covered with aluminum foil and stored in the biosafety cabinet overnight. A glass vacuum filtration unit was used for filtration of 1 L water samples. The components of the unit were covered with aluminum foil and sterilized using the autoclave. The disposable nitrocellulose filter membranes (product no. HAWG04705, EMD Millipore, Danvers, Mass., USA) used in the glass filtration unit were also sterilized using the autoclave. A bacteria suspension was prepared by spiking bacteria into 50 mL reagent grade water using a disposable inoculation loop from a TSA plate containing *E. coli* colonies. The suspension was mixed gently to have uniform distribution of bacteria. Three TSA plates, 3 ECC ChromoSelect Selective Agar plates, 4 CHROMagar™ ECC plates were removed from refrigerator and kept at room temperature for 30 min.

Three bottles of 120 mL disposable vessels with sodium thiosulfate (product no. WV120SBST-200, IDEXX Laboratories Inc., Westbrook, ME, USA) were filled with 100 mL filter sterilized reagent grade water. 0.1 mL of bacterial suspension was spiked into 1 L water sample, 1.2 L water sample (1 L water+0.2 L concentrated broth), 3 bottles of 100 mL water samples, 3 TSA plates and 3 ECC ChromoSelect Selective Agar plates, sequentially. The timer was started immediately after adding the spike into the suspensions.

Figure 15:
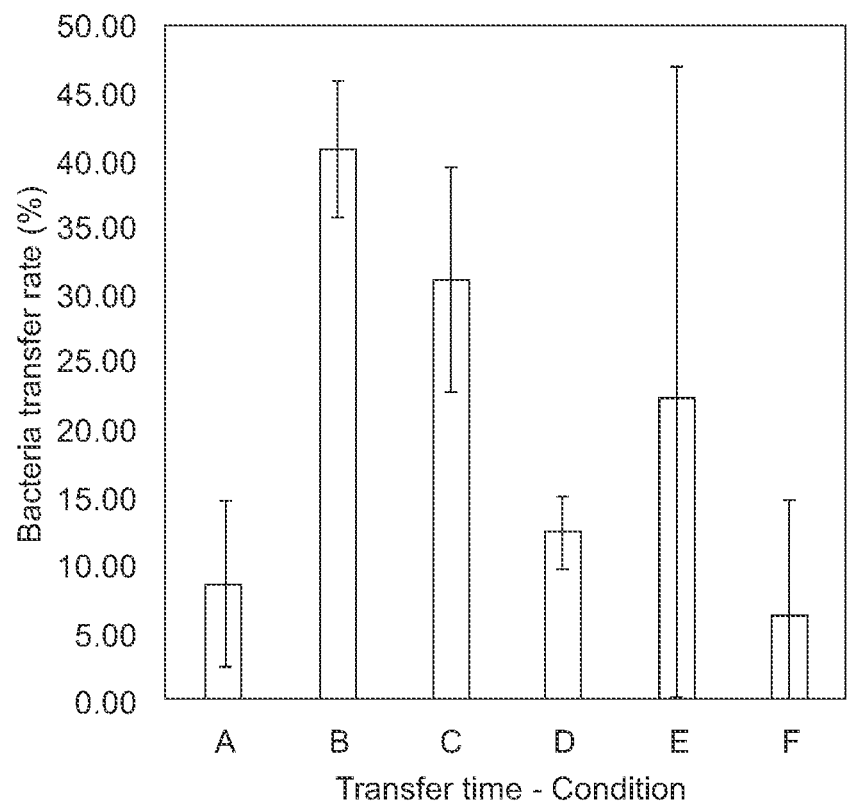
FIG. 15 illustrates a graph of bacteria transfer rate (%) obtained at different conditions of transfer time.

First, the suspensions on TSA plates and ECC ChromoSelect Selective Agar were spread using L-shaped disposable spreaders. Then, the water sample with broth was mixed for about a minute and then stored in 35° C. for 5 h. One Colilert® 18 reagent (product no. 98-27164-00, IDEXX Laboratories Inc., Westbrook, ME, USA) was added into each 100 mL bacterial suspension and the mixture was shaken. The content of bottle was poured into a Quanti-Tray 2000 bag (product no. 98-21675-00, IDEXX Laboratories Inc., Westbrook, ME, USA) and after removing bubbles in each well, the bag was sealed using Quanti-Tray Sealer (product no. 98-09462-01, IDEXX Laboratories Inc., Westbrook, ME, USA). Three bags sealed and labelled with the experiment details were incubated at 35° C. for 18 h. Next, 30 mL filtered reagent grade water was used to moisturize the membrane in the glass filtration unit and then *E. coli* contaminated 1 L water sample was filtered at a pressure of 50 kPa. The bottle was rinsed using 150 mL of sterilized reagent grade water and the solution was filtered on the unit (FIG. 14). The funnel was rinsed using 50 mL of sterilized reagent grade water twice. After the filtration was complete, the membrane was removed and placed onto a CHROMagar™ ECC plate face down. Gentle pressure was applied on the membrane using a tweezer to remove any air bubbles between the agar and the membrane. Then, a 30 g of weight was put on the membrane to provide continuous pressure during the transfer of bacteria from the membrane to the agar plate (FIG. 15). After 5 min of incubation, the membrane was peeled off from the agar surface gently and put into another agar facing up. The agar containing the membrane was incubated at the benchtop incubator at 35° C. and the agar containing the transferred bacteria was incubated at the lens-free imaging platform for time-lapse imaging. After 5 h of incubation, the bottle containing 1.2 L suspension was filtered using the same procedure as described before for filtration of 1 L sample. The agar plate containing the transferred bacteria was incubated at the second sample tray of the lens-free imaging setup for time-lapse imaging while the agar containing the membrane was incubated at the benchtop incubator.

Design of the High-Throughput Time-Resolved Microorganism Monitoring Platform

The platform (used for the experiments herein) consists of five modules: (1) a holographic imager device 12, (2) a mechanical translational system 22, (3) an incubator 16, (4) control circuitry 26, and (5) a controlling program 28. Each module is explained in detail below.

Fiber-coupled partially-coherent laser illumination (SC400-4, Fianium Ltd, Southampton, UK) was used as the illumination source 18, with wavelength and intensity controlled through an acousto-optic tunable filter (AOTF) device (Fianium Ltd, Southampton, UK). The device 18 is remotely controlled with a customized program written in the C++ programming language, and runs on a controlling laptop computer 82 (product no. EON17-SLX, Origin PC). The laser light is transmitted through the sample, i.e., the agar plate that contains the bacterial colonies 102, and forms an inline hologram on a CMOS image sensor 20 (product no. acA3800-14 µm, Basler AG, Ahrensburg, Germany) with a pixel size of 1.67 µm and an active area of 6.4 mm×4.6 mm. The CMOS image sensor 20 is connected to the same controlling laptop computer 82 through a universal serial bus (USB) 3.0 interface and is software-triggered within the same C++ program. The exposure time at each scanning position is pre-calibrated according to the intensity distribution of the illumination light, and ranges from 4 ms to 167 ms. The images 70*h* are saved as 8-bit bitmap files for further processing.

The mechanical stage 24 is customized with a pair of linear translation rails 44 (Accumini 2AD1OAAAHL, Thomson, Radford, VA, USA), a pair of linear bearing rods 40 (8 mm diameter, generic), and linear bearings (LM8UU, generic), and it is aided by parts printed by a 3D printer for the joints, housing, and feet 60, 66 (Objet30 Pro, Stratasys, Minn., USA). The two-dimensional horizontal movement is powered by two stepper motors 52, 54 (product no. 1124090, Kysan Electronics, San Jose, Calif., USA)—one for each direction, and these motors 52, 54 are individually controlled using stepper motor controller chips (DRV8834, Pololu Las Vegas, NV, US). To minimize the backslash effect, the whole Petri dish, which functions as the growth plate 14, is scanned following the raster scan pattern.

The incubator 16 is built with the top heating plate of a microscope incubator (INUBTFP-WSKM-F1, Tokai Hit, Shizuoka, Japan), and it is housed by a 3D frame printed by a 3D printer. The Petri dish containing the sample is placed on the heating plate with the surface having bacteria facing downwards. The temperature is controlled by a paired controller that maintains a temperature of 47° C. on the heating plate, resulting in a temperature of 38° C. inside the Petri dish.

The control circuit 26 consists of three components: a micro-controller (Arduino Micro, Arduino LLC) communicating with the computing device 82 through a USB 2.0 interface, two stepper motor driver chips (DRV8834, Pololu Las Vegas, NV, US) externally powered by a 4.2 V constant voltage power supply (GPS-3303, GW Instek, Montclair, CA, US), and a metal—oxide—semiconductor field-effect transistor (MOSFET)-based digital switch (SUP75P03-07, Vishay Siliconix, Shelton, Conn., United States) for controlling the CMOS sensor connection.

The controlling program 28 includes a graphical user interface (GUI) and was developed using the C++ programming language. External libraries including Qt (v5.9.3), AOTF (Gooch & Housego), and Pylon (v5.0.11) were integrated.

Data Acquisition

Inoculated agar plates of pure bacterial colonies were prepared (see the Sample Preparation description under the Methods for details), and captured images of an entire agar plate at 30-minute intervals. The illumination light was set to a wavelength of 532 nm and an intensity of ~400 µW. To maximize the image acquisition speed, the captured images were first saved into a computer memory buffer and then written to hard disk by another independent thread. At the end of each experiment (i.e., after 24 h of incubation), the sample plate was imaged using a benchtop scanning microscope (Olympus IX83) in reflection mode, and the resulting images were automatically stitched to a full-FOV image, used for comparison. Subsequently, the plate was disposed of as solid biohazardous waste. Data (i.e., time-lapse lens-free images) was populated corresponding to ~6,969 *E. coli*, ~2,613 *K. aerogenes*, and ~6,727 *K. pneumoniae* individual bacterial colonies to train and validate the models. Another 965 colonies of three (3) different species from fifteen (15) independent agar-plates 14 were used to blindly test the machine learning models 90, 92.

Image Processing and Analysis

The acquired lens-free images 70*h* are processed using custom-developed image processing and deep learning algorithms. There are five major image processing steps for the early detection and automated classification and counting of colonies. These steps are described in detail below.

Image stitching to obtain the image of the entire plate area: Following the acquisition of holographic images 70*h* using the multi-threading approach, all the images 70*h* within a tile-scan of the whole Petri dish per wavelength are merged into a single full-FOV image. During a tile scan, the images 70*h* are acquired with ~30% overlap on each side of the image 70*h*, to calculate the relative image shifts against each other. As for each image 70*h*, the relative shifts against all four of the neighboring images are calculated using a phase correlation method, followed by an optimization step that minimizes an object function, as defined by:

$$\operatorname*{argmin}_{T_{VF}} \sum_{A \in V \setminus \{F\}} \left( \sum_{B \in V \setminus \{F\}} \left\| \vec{t}_{AF} - \vec{t}_{BF} - \vec{p}_{AB} \right\|^2 \right), \quad (1)$$

where V is the set of all tile images, F ∈ V is a fixed image, e.g., the image captured at the center of the sample Petri dish, $\vec{t}_{AB}$ stands for the relative position of image A with respect to image B, and $\vec{P}_{AB}$ is the local shift between images A and B, calculated by the phase correlation method using the overlapping regions of the two neighboring images, which can be formulated as:

$$\vec{p}_{AB} = (\Delta x, \Delta y) = \operatorname*{argmax}_{(x,y)} F^{-1} \left\{ \frac{F\{A\} \cdot F\{B\}^*}{|F\{A\} \cdot F\{B\}^*|} \right\} \quad (2)$$

where F is the Fourier transform operator and $F^{-1}$ is the inverse Fourier transform operator. The optimal configuration $T_{VF} = \{\vec{t}_{AF}: A, F \in V\}$ represents the relative positions of all the images with respect to the fixed image F and it is used as the global position of each tile image 70*h* for full-FOV image stitching. To eliminate tiles with a low signal-to-noise ratio (SNR) that lead to incorrect local shift estimation values, a correlation threshold of 0.3 is applied during the optimization, meaning that if the cross-correlation coefficient of the overlapped parts of two images is below 0.3, the shift calculation is discarded. Once the positions of all of the tile images 70*h* are obtained, they are merged into a full FOV image of the whole Petri dish using linear blending. A full-FOV image of the whole Petri dish is defined as a 'frame'. All the frames are normalized so that the mean value is 50, and they are saved as unsigned 8-bit integer (0-255) arrays.

Colony candidate selection by differential analysis: When a new frame is acquired at time t, it is cross-registered to the previous frame at time t−1, and then is digitally back-propagated to the sample plane to obtain the complex light field $$\tilde{B}_t = P(F_t, z), \quad (3)$$

where $F_t$ is the frame at time t, z is a surface normal vector of the sample plane obtained by digital auto-focusing at 50 randomly-spaced positions, and P denotes the angular spectrum-based back-propagation operation used for image reconstruction. Details regarding reconstruction may be found in Greenbaum et al., Wide-field computational imaging of pathology slides using lens-free on-chip microscopy. *Science Translational Medicine* 6, 267ra175-267ra175 (2014), which is incorporated by reference herein. To accommodate the large FOV of a stitched frame (36000× 36000 pixels), digital back-propagation is performed with 2048×2048-pixel blocks, which are then merged together to generate the reconstructed image 70*r*.

Four consecutive frames were taken, i.e., from t−3 to t, and calculate a differential image defined by:

$$D_t = HP \left[ LP \left( \frac{1}{3} \sum_{\tau=t-2}^{t} |\tilde{B}_\tau - \tilde{B}_{\tau-1}| \right) \right], \quad (4)$$

where $D_t$ is the differential image at time t, $\tilde{B}_t$ represents the complex light field obtained by back-propagating frame t, and LP and HP represent low-pass and high-pass image filtering, respectively. The HP filter removes the differential signal from a slowly-varying background (unwanted term), and the LP filter removes the high-frequency noise-introduced spatial patterns. The LP and HP filter kernels are empirically set to 5 and 100, respectively.

Following the differential image calculation, regions in the differential image with >50 connective pixels were selected that are above an intensity threshold, which is empirically set to 12. These regions are marked as colony candidates, as they give a differential signal over a period of time (covering four consecutive frames). However, some of the differential signal comes from non-bacterial objects, such as a water bubble or surface movement of the agar itself. Therefore, two DNNs 90, 92 were used to select the true candidates (DNN 90) and classify (DNN 92) their species.

Figures 16B, 16C:
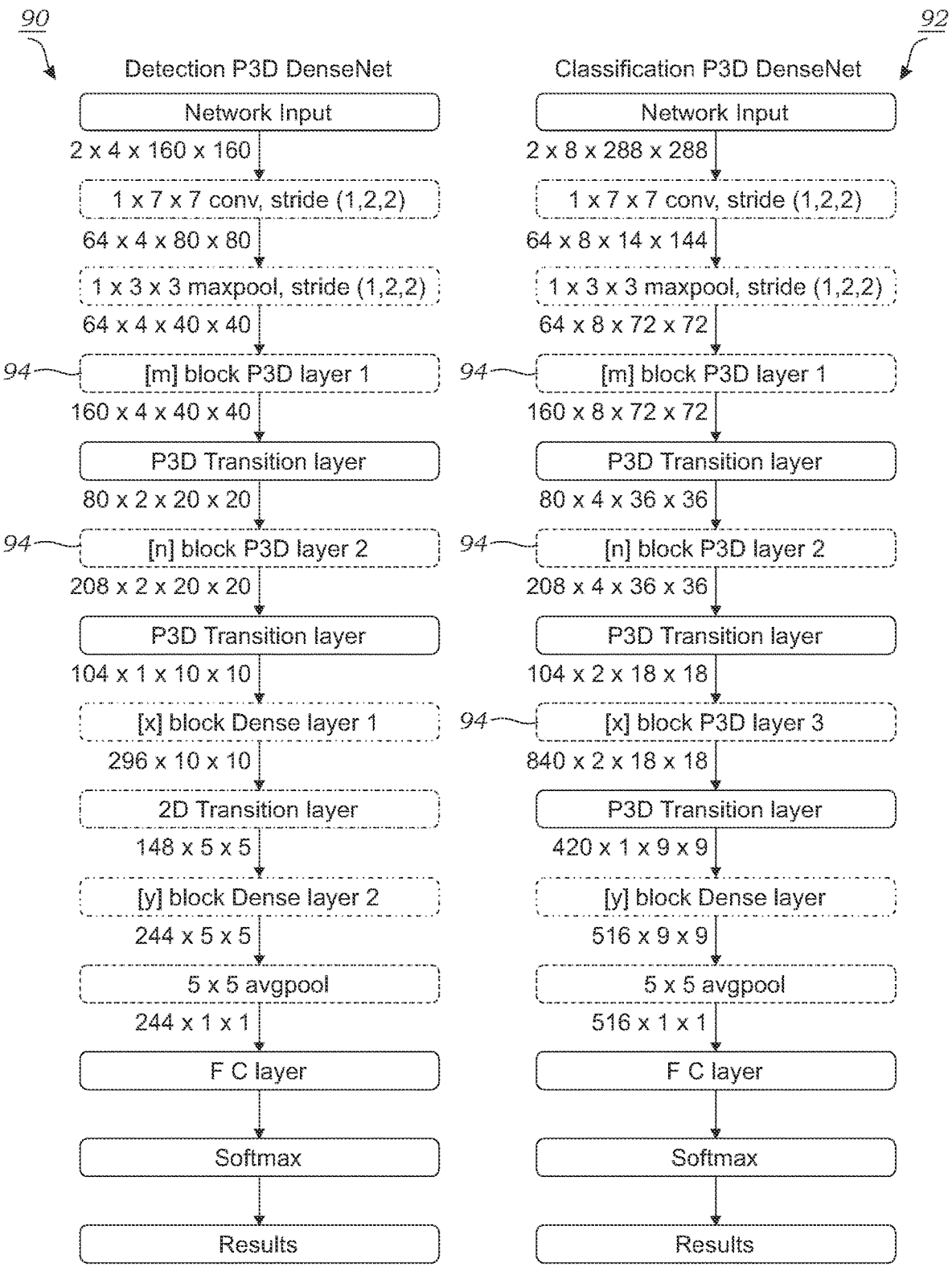

DNN-enabled detection of growing bacterial colonies: Following the colony candidate selection process outlined earlier, candidate regions of 160×160 pixels (~267×267 µm²) were cropped out across the four back-propagated consecutive frames and separate the complex field into amplitude and phase channels. Therefore, each candidate region is represented by a 2×4×160×160 array. This four-dimensional (phase/amplitude-time-x-y) data format differs from the traditional three-dimensional data used in image classification tasks and requires a custom-designed DNN architecture that accounts for the additional dimension of time. The DNN 90 was designed by following the block diagram of DenseNet, and replaced the 2D convolutional layers with P3D convolutional layers 94, as shown in FIG. 16B. The network 90 was implemented in Python (v3.7.2) with the PyTorch Library (v1.0.1). The network 90 was randomly initialized and optimized using an adaptive moment estimation (Adam) optimizer with a starting learning rate of 1×10' and a batch size of 64. To stabilize the accuracy of the network model 90, a learning rate-scheduler was set that decayed the learning rate by half every 20 epochs. Approximately 16,000 growing colonies and 43,000 non-colony objects captured from 71 agar plates were used in the training and validation phases. The best network model 90 was selected based on the best validation accuracy. Data augmentation was also applied by random 90°-rotations and flipping operations in the spatial dimensions. The whole training process took ~5 h using a desktop computer with dual GPUs (GTX1080Ti, Nvidia). The decision threshold value after the softmax layer was set to 0.5 during training, i.e., positive for softmax value >0.5 and negative for softmax value <0.5, which implies equal penalty to false positive and false negative events. The threshold value was set to 0.99, empirically based on the training dataset before blind testing, to favor less false positive events.

DNN-enabled classification of bacterial colony species: Once the true bacterial colonies are selected using the DNN 90, they grow for another 2 h to collect 8 consecutive frames, i.e., 4 h, and then are sent to the second DNN 92 as a 2×8×288×288 array for classification of colony species (FIG. 16C). To perform the classification task, this time, the training data only contain the true microorganism colonies 102 and their corresponding species (ground truth). The network 92 follows a similar structure and training process as the detection model, as illustrated in FIG. 16B. The network 92 was randomly initialized and optimized using the Adam optimizer, with a starting learning rate of $1\times10^{-4}$ and a batch size of 64. The learning rate decayed by 0.9 times every 10 epochs. To avoid overfitting to a specific plate, colony images extracted from extremely dense samples (>1000 CFU per plate) were discarded. As a result, approximately 9,400 growing colonies 102 were used in the training and validation of the classification model. The whole training process took ~15 h using a desktop computer with dual GPUs (GTX1080Ti, Nvidia).

Colony counting: The respective ground truth information on the growing colonies in each experiment was created after the sample is incubated for >24 h. At the boundary of the plate, the agar always forms a curved surface owing to surface tension, thereby distorting the images of the colonies. Therefore, the effective imaging area was limited to a 50 mm-diameter circle in the center of the agar-plate 14. In the cases, where multiple colonies 102 are closely spaced and eventually merge into one large colony 102 (e.g., toward the end of 24 h incubation period), the lens-free time-lapsed images were then used to verify the true colony number when detected by the method, so as to avoid over-counting.

Calculation of Imaging Throughput

In Table 2, the imaging throughput of the system 10 was compared with a conventional lens-based scanning microscope in terms of the space-bandwidth product (SBP) using the following formula:

$$N_1 = \alpha \cdot FOV \cdot r^2 / \delta^2 \qquad (5)$$

where $N_1$ is the effective pixel-count of a frame, $\delta$ is the half-pitch resolution, r is the digital sampling factor along the x and y directions, and $\alpha=2$ represents the independent spatial information contained in the phase and amplitude images of the holographic reconstruction, while $\alpha=1$ represents the amplitude-only information contained in an image captured using the standard lens-based bright-field scanning microscope. In the lens-based microscope, a color camera was used with a pixel size of 7.4 µm. Therefore, for a 4× objective lens the image resolution is limited to ~3.7 p.m, owing to the Nyquist sampling limit. Without loss of generality, r =2.

While embodiments of the present invention have been shown and described, various modifications may be made without departing from the scope of the present invention. For example, in one alternative embodiment, the image sensor(s) 20 may remain stationary while the growth plate(s) 14 is/are moved relative the image sensor(s) 20. Any relative movement between the image sensor(s) 20 and the growth plate(s) 14 will work. In addition, in some embodiments, the image sensor 20 does not need to be scanned at all and may remain stationary to obtain the time-lapsed images (e.g., a large image sensor). Various actuators, robotic arms, motors, servos, can be implemented to impart this relative movement between the image sensor(s) 20 and the growth plate(s) 14. In addition, in some embodiments a lens or set of lenses may be used to magnify or de-magnify the image(s) 70h captured by the image sensor(s) 20. The invention, therefore, should not be limited, except to the following claims, and their equivalents.

What is claimed is:

1. A system for the early detection and classification of live microorganisms in a sample using time-lapse imaging comprising:
   a partially-coherent or fully coherent light source;
   an incubator configured to hold one or more growth plates therein or thereon containing the sample and disposed along an optical axis from the light source;
   a translation stage having mounted thereon at least one image sensor and/or the one or more growth plates, the translation stage configured to move the at least one image sensor and/or the one or more growth plates along one or more dimensions to capture time-lapse holographic images of microorganisms on the one or more growth plates with the at least one image sensor;

control circuitry configured to drive the translation stage;

image processing software configured to process and analyze time-lapse holographic images of the microorganisms or clusters of microorganisms on the one or more growth plates; and a computing device configured to execute the image processing software thereon and receive the captured time-lapse holographic images of the microorganisms on the one or more growth plates, the image processing software configured to detect candidate microorganism colonies in the time-lapse holographic images based on differential image analysis in the time-lapse holographic images or reconstructed images thereof and further including a first trained deep neural network configured to detect true microorganism colonies from non-microorganism objects in the detected candidate microorganism colonies and a second trained deep neural network that receives as an input at least one time-lapsed holographic image or reconstructed image and/or at least one digitally processed time-lapsed image of the true microorganism colonies and outputs a species associated with each of the detected true microorganism colonies.

2. The system of claim 1, wherein the microorganisms comprise a prokaryotic cell, a eukaryotic cell, bacteria, fungi, virus, multi-cellular organism or clusters or films thereof.

3. The system of claim 1, wherein the computing device comprises a local and/or remote computing device(s).

4. The system of claim 1, wherein the incubator comprises one or more heaters and control circuitry configured to maintain the incubator or the one or more growth plates contained therein or thereon at a setpoint temperature or setpoint temperature range.

5. The system of claim 1, further comprising a humidity controller unit and control circuitry configured to maintain the one or more growth plates contained therein at a setpoint humidity level or setpoint humidity level range.

6. The system of claim 1, wherein the translation stage is configured to scan the one or more growth plates in one or more directions or scan the at least one image sensor in one or more directions.

7. The system of claim 1, wherein differential images are obtained by digitally back-propagating a set of acquired time-lapse holographic images to at least one sample plane to create multiple consecutive images of the same region under test within the one or more growth plates.

8. The system of claim 1, wherein the first and/or second trained deep neural network is/are configured to output a microorganism colony count or microorganism colony concentration within the sample under test.

9. The system of claim 1, wherein a lens or set of lenses are used to magnify or de-magnify holograms of the microorganisms and/or colonies thereof onto the at least one image sensor.

10. The system of claim 1, wherein the translation stage moves the at least one image sensor and/or the one or more growth plates along two dimensions.

11. A method of using the device of claim 1, comprising:
placing one or more growth plates comprising the sample in or on the incubator;
illuminating the one or more growth plates with the light source; and
periodically scanning the at least one image sensor and/or the one or more growth plates with the translation stage to obtain a plurality of time-lapsed holographic images of the one or more growth plates.

12. The method of claim 11, further comprising processing the time-lapsed holographic images or reconstructed images thereof of the one or more growth plates with the image processing software.

13. The method of claim 12, wherein the image processing software is further configured to output a microorganism colony count or microorganism colony concentration of the sample.

14. The method of claim 12, wherein the microorganisms comprise a prokaryotic cell, a eukaryotic cell, bacteria, fungi, virus, multi-cellular organism or clusters or films thereof.

15. The method of claim 12, wherein the image processing software is executed on a local computing device and/or a remote computing device.

16. The method of claim 11, wherein the sample comprises one or more of a water sample, a food sample, a biological or other fluid sample.

17. A method of detecting and classifying live microorganisms using time-lapse imaging comprising:
loading one or more growth plates containing a sample into or onto an incubator;
illuminating the one or more growth plates with a partially-coherent or fully coherent light source;
periodically scanning: (1) at least one image sensor and/or (2) the one or more growth plates along one or more dimensions with a translation stage to capture holographic images of microorganisms on the one or more growth plates;
capturing a plurality of image tiles of the one or more growth plates with the at least one image sensor for each periodic scanning operation;
digitally stitching the plurality of image tiles from the periodic scans to generate a full field-of-view (FOV) time-lapsed images of the one or more growth plates with image processing software;
registering full FOV time-lapsed images of the one or more growth plates obtained over different time periods with the image processing software; and
detecting candidate microorganism colonies in the registered time-lapse images with the image processing software based on differential image analysis in the registered time-lapse images and further including a first trained deep neural network configured to detect true microorganism colonies from non-microorganism objects and a second trained deep neural network that receives as an input at least one time-lapsed image and/or at least one digitally processed time-lapsed image and outputs a species associated with each one of the detected true microorganism colonies.

18. The method of claim 17, wherein the sample is pre-incubated with one or more culture media prior to transfer into the one or more growth plates.

19. The method of claim 17, wherein the microorganisms comprise a prokaryotic cell, a eukaryotic cell, fungi, bacteria, virus, multi-cellular organism or clusters or films thereof.

20. The method of claim 17, wherein the periodic scans are performed multiple times each hour over several hours.

21. The method of claim 17, wherein the at least one image sensor captures magnified or de-magnified holograms of the microorganism objects and/or microorganism colonies thereof using a lens or set of lenses.

22. A method of detecting and classifying live microorganisms using time-lapse imaging comprising:
- loading one or more growth plates containing a sample into an incubator;
- illuminating the one or more growth plates with a partially-coherent or fully coherent light source;
- capturing time-lapse holographic images of the microorganisms on the one or more growth plates;
- reconstructing time-lapsed images from the captured time-lapse holographic images; and
- detecting candidate microorganism colonies in the reconstructed time-lapse images with image processing software based on differential image analysis in the reconstructed time-lapse images and further including a first trained deep neural network configured to detect true microorganism colonies from non-microorganism objects and a second trained deep neural network that receives as an input at least one reconstructed time-lapsed image and/or at least one digitally processed time-lapsed image and outputs a species associated with each one of the detected true microorganism colonies.

23. A system for the early detection and classification of live microorganisms using time-lapse imaging comprising:
- a partially-coherent or fully coherent light source;
- an incubator configured to hold one or more growth plates therein or thereon containing a sample and disposed along an optical axis from the light source;
- a translation stage having mounted thereon at least one image sensor and/or the one or more growth plates, the translation stage configured to move the at least one image sensor and/or the one or more growth plates along one or more dimensions to capture time-lapse holographic images of microorganisms on the one or more growth plates;
- control circuitry configured to drive the translation stage; and
- at least one computing device configured to receive the captured time-lapse holographic images of the microorganisms on the one or more growth plates and comprising image processing software configured to detect candidate microorganism colonies in the time-lapse holographic images or reconstructions thereof based on differential image analysis in the time-lapse images and further including a trained deep neural network configured to detect true microorganism colonies from non-microorganism objects as well as output a species associated with each of the detected true microorganism colonies.

24. A method of detecting and classifying live microorganisms using time-lapse imaging comprising:
- loading one or more growth plates containing a sample into an incubator;
- illuminating the one or more growth plates with a partially-coherent or fully coherent light source;
- capturing time-lapse holographic images of microorganisms on the one or more growth plates; and
- detecting candidate microorganism colonies in the time-lapse holographic images or reconstructions thereof with image processing software based on differential image analysis in the time-lapse images and further including a trained deep neural network configured to detect true microorganism colonies from non-microorganism objects as well as output a species associated with each one of the detected true microorganism colonies.

* * * * *